(12) United States Patent
Chen et al.

(10) Patent No.: US 11,898,010 B2
(45) Date of Patent: Feb. 13, 2024

(54) POLYIMIDES, KETONE-CONTAINING ALICYCLIC DIANHYDRIDES AND APPLICATIONS THEREOF

(71) Applicant: National Taiwan University of Science and Technology, Taipei (TW)

(72) Inventors: Jyh-Chien Chen, Hsinchu (TW); Hsiang Jung Lee, Taipei (TW); Kai-Cheng Zhong, Kaohsiung (TW)

(73) Assignee: National Taiwan University of Science and Technology, Taipei (TW)

( * ) Notice: Subject to any disclaimer, the term of this patent is extended or adjusted under 35 U.S.C. 154(b) by 277 days.

(21) Appl. No.: 17/383,782

(22) Filed: Jul. 23, 2021

(65) Prior Publication Data
US 2022/0372228 A1    Nov. 24, 2022

(30) Foreign Application Priority Data
May 7, 2021    (TW) .................. 110116598

(51) Int. Cl.
*C08G 73/10* (2006.01)
*C09D 179/08* (2006.01)
*C07D 493/08* (2006.01)
*C08J 5/18* (2006.01)

(52) U.S. Cl.
CPC ....... *C08G 73/1078* (2013.01); *C07D 493/08* (2013.01); *C08G 73/1007* (2013.01); *C08J 5/18* (2013.01); *C09D 179/08* (2013.01); *C08J 2379/08* (2013.01)

(58) Field of Classification Search
CPC ......... C08G 73/10; C08G 73/1007; C08J 5/18
See application file for complete search history.

(56) References Cited

FOREIGN PATENT DOCUMENTS

JP    2010184898    *  8/2010

OTHER PUBLICATIONS

USPTO structure search, Jun. 2023.*

* cited by examiner

*Primary Examiner* — Gregory Listvoyb
(74) *Attorney, Agent, or Firm* — Best & Flanagan LLP

(57) ABSTRACT

Present invention is related to a polyimide of formula as following:

formula

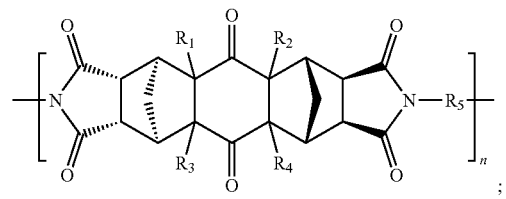

and
a ketone-containing alicyclic dianhydride of formula as following:

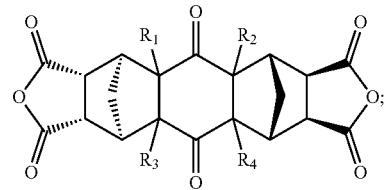

wherein:
R1, R2, R3, R4 denote hydrogen atom or carbon containing functional group with carbon number at a range of 1-4; R5 denotes diamine group; and n equals to any positive integer.

5 Claims, 16 Drawing Sheets

POLYIMIDES, KETONE-CONTAINING ALICYCLIC DIANHYDRIDES AND APPLICATIONS THEREOF

FIELD OF INVENTION

Present invention is related to a polyimide and a novel ketone-containing alicyclic dianhydrides for producing the said polyimide and applications thereof.

BACKGROUND OF THE INVENTION

Polyimide (PI) is a polymer with excellent thermal and mechanical properties as it is widely used in the industry nowadays. PI has two variants derivatizing from aromatic and aliphatic chemical structures. Particularly to the optoelectronic industry, conventional aromatic polyimides normally has color which cannot be introduced of making transparent optical films. Aliphatic polyimide otherwise is more suitable for producing transparent optical films with its transparency and lower charge transfer interaction on such use. However, synthesis process of aliphatic monomers for manufacturing aliphatic polyimides has problem of isomers and other by-products which become more difficult to separate and purify for determine the actual structure of synthesized compounds. These uncontrollable factors result in the limitation of use for aliphatic polyimides. Therefore, a refine synthesis path of such monomer has become one of the most critical point in the development of aliphatic polyimides. It is eager to have a solution that will overcome or substantially ameliorate at least one or more of the deficiencies of a prior art, or to at least provide an alternative solution to the problems. It is to be understood that, if any prior art information is referred to herein, such reference does not constitute an admission that the information forms part of the common general knowledge in the art.

SUMMARY OF THE INVENTION

In order to solve the problem that conventional aromatic polyimides cannot be used in transparent optical films. The aliphatic polyimides also struggle from the difficulties for the separation and purification the by-products in the producing process. The present invention provides a new type of ketone-containing alicyclic dianhydride monomer by series of new synthesis paths, and successfully synthesizes the polyimide by using such novel monomers having excellent thermal stability, mechanical strength, size stability, solubility and transparency.

According to a first aspect of the present invention, a polyimide comprises repeated structure as below formula (1):

formula (1)

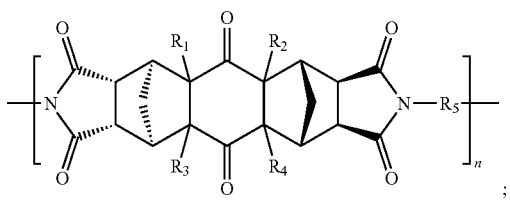

wherein in formula (1):
R1, R2, R3 and R4 represent hydrogen atom and/or carbon containing functional group including C1 to C4 alkanes;
R5 represents diamine functional group; and
n represents any positive integer.

In accordance, in formula (1) where R1, R2, R3 and R4 further comprises at least one of below stereoisomer as formula (2) and formula (3):

formula (2)

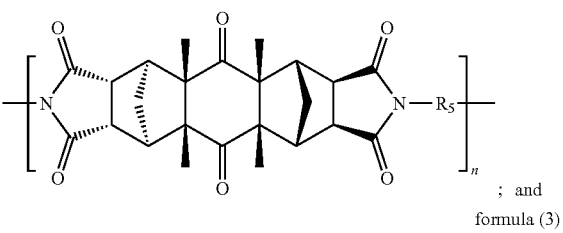

; and formula (3)

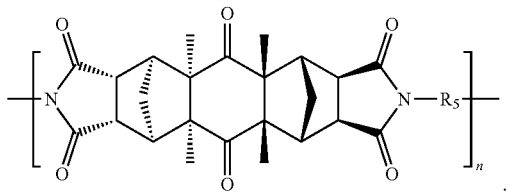

In accordance, the diamine functional group comprises aromatic diamine or aliphatic diamine.

In accordance, the aromatic diamine and aliphatic diamine comprise 4,4'-bis(aminophenyl)ether and 2,2'-bis(trifluoromethyl)benzidine.

In accordance, the second aspect of the present invention, a ketone-containing alicyclic dianhydride for producing abovementioned polyimide comprises a chemical structure as formula (4):

formula (4)

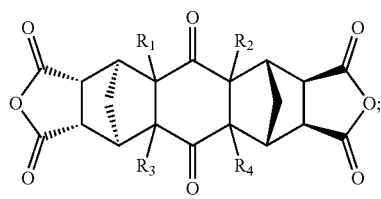

wherein, R1, R2, R3 and R4 represent hydrogen atom and/or carbon containing functional group including C1 to C4 alkanes.

In accordance, in formula (4) where R1, R2, R3 and R4 further comprises at least one of below stereoisomer as formula (5) and formula (6):

formula (5)

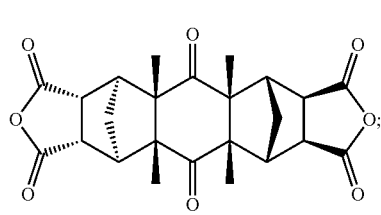

-continued formula (6)

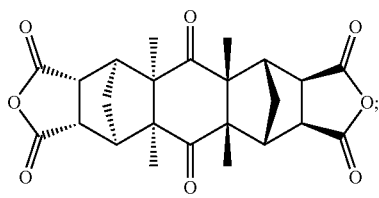

In accordance, the present invention also provides a solution for making a thin film comprising the aforementioned polyimide and an organic solvent.

In accordance, the aforementioned polyimide could be utilized in various uses as thin membrane, film or coat in different applications.

In accordance, the present invention has the following advantages:

In the production process, the present invention initiates from benzoquinone compounds for Diels-Alder reaction. By going through nucleophilic substitution reaction and methoxycarbonylation reaction, the present invention has successfully syntheses a series of novel aliphatic dianhydride containing ketone-group. The present invention also determines the configuration of dianhydride by single crystal XRD diffraction. This series of polymers have been tested and verified to show excellent thermal properties, mechanical properties, size stability, solubility and transparency to the final film product.

The present invention uses a variety of analytical instruments to identify and determine the structure and configuration of the compound including nuclear magnetic resonance spectroscopy ($^1$H NMR, $^{13}$CNMR), two-dimensional map ($^1$H, $^1$H-COSY, $^{13}$C, $^1$H-HSQC), elemental analysis, MASS spectrometer (EI-Mass), single crystal XRD diffraction analysis. Taking the PI-5b-a of polyimide polymer synthesized form aliphatic dianhydride CTMDA (5b) and 4,4'-oxydianiline (4,4'-ODA) disclosed in the present invention as an example, the $Td_{5\%}$ of this PI-5b-a is 470° C., Tg is 460° C., and CTE is 38.8 ppm/° C. Compared to other conventional aliphatic polyimides, the present invention has higher $Td_{5\%}$, Tg, and lower coefficient of thermal expansion (CTE), showing better thermal properties. Also, the PI polymer also shows excellent mechanical properties including the Young's modulus of PI-5b-a is 1.66 GPa, the tensile strength is 35.1 MPa and the strain is 6% indicating that the polyimide of the present invention has good size stability. It has been verified that the polyimide PI-5c-a in 12 μm thin film in preferred embodiment of the present invention has the most remarkable and excellent optical properties with $\lambda_{cut-off}$ wavelength of 284 nm and a transmittance rate of 86.68% in wavelength of 400 nm. The series of polyimide PI-5a-a, PI-5b-a, PI-5c-a, PI-5a-b, PI-5b-b, PI-5c-b are soluble in all polar non-protic solvents at room temperature, especially for the polyimide PI-5a-b, PI-5b-b, and PI-5c-b can be dissolved in tetrahydrofuran (THF) and acetone at room temperature. Furthermore, the dianhydride monomer provided by the present invention has five interconnected three-dimensional structures of exo-exo-syn-endo-exo or exo-endo-anti-endo-exo for better Tg performance compared with the conventional dianhydride monomers.

Many of the attendant features and advantages of the present invention will become better understood with reference to the following detailed description considered in connection with the accompanying figures and drawings.

BRIEF DESCRIPTION OF THE DRAWINGS

The steps and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

Figure 1:
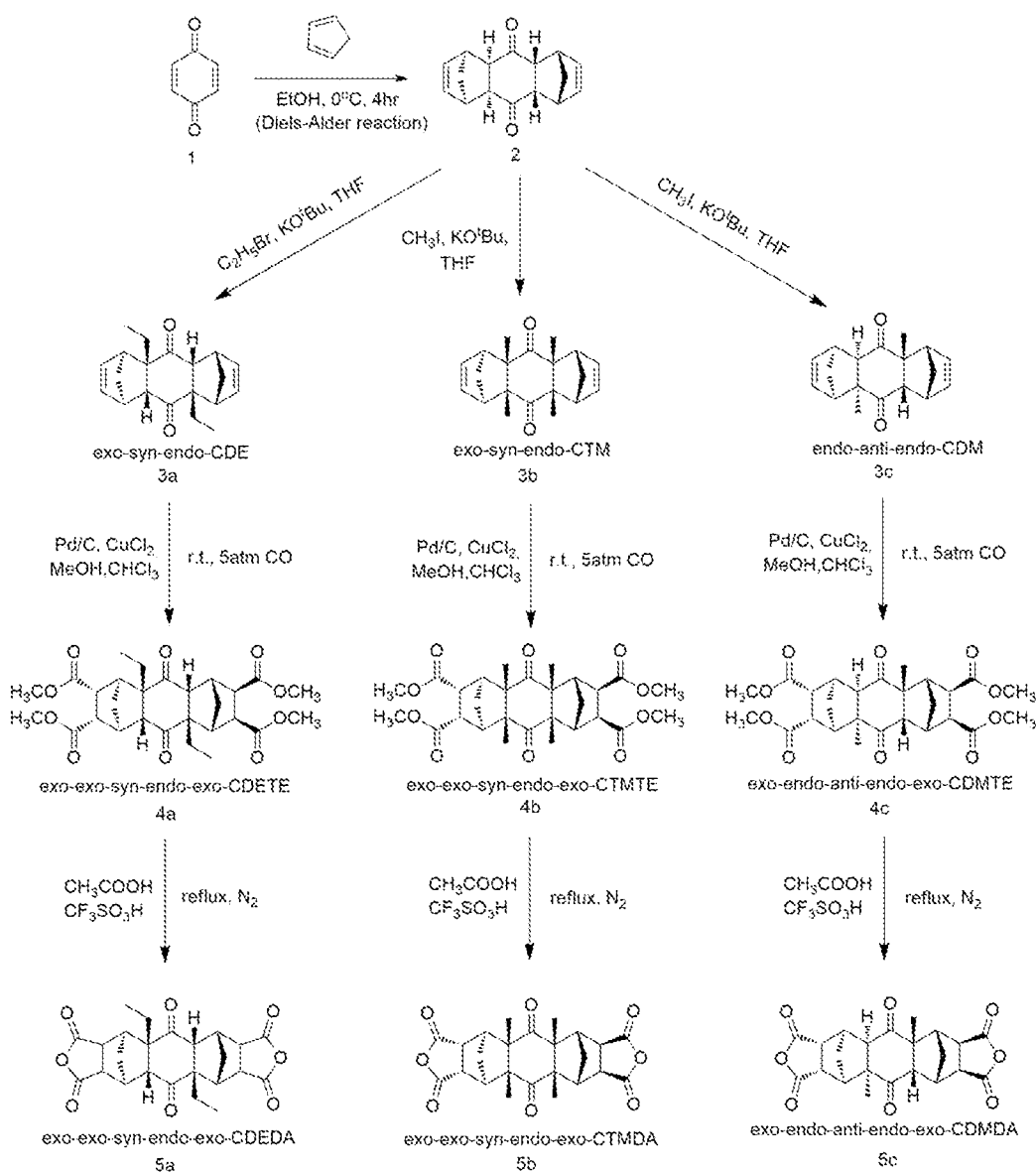
FIG. 1 is a flow chart showing one of a preferable embodiment of the synthesis process for producing the novel ketone-containing alicyclic dianhydrides series monomers and the polyimide in Formulas (1)-(6) in accordance with the present invention.

Reference will now be made in detail to the present preferred embodiments of the invention, examples of which are illustrated in the accompanying drawings. Wherever possible, the same reference numbers are used in the drawings and the description to refer to the same or like parts. It is not intended to limit the method by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details. As used in the description herein and throughout the claims that follow, the meaning of "a", "an", and "the" may include reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to.

To facilitate of understanding and reading the present invention, all the following process of synthesis of this novel ketone-containing alicyclic dianhydrides will be described in sequence. However, it should be understandable yet more reasonable that the process of synthesis provided below is only preferable embodiments. Other reasonable adjustments in the same or similar process or steps shall be covered by the present invention.

With referent to FIG. 1, which is a flow chart showing one of preferable embodiment of the synthesis process for producing the novel ketone-containing alicyclic dianhydrides series monomers and a preferred embodiment of the polyimide polymer described in Formulas (1)-(6) above. This preferred embodiment of the present invention mainly provide three kinds of alicyclic dianhydrides monomers, including alicyclic dianhydrides monomer 5a, 5b and 5c, as shown in FIG. 1, and having the stereoisomerism characteristic of Formulas (5) and (6) shown above.

Chemical Compound 2—(1R,4S,4aR,5S,8R,8aS, 9aS,10aR)-1,4,4a,5,8,8a,9a,10a-° C.tahydro-1,4:5,8-dimethanoanthracene-9,10-dione To obtain chemical compound 2 in this embodiment, the synthesis steps are as following:

adding 6.0 g 1,4-benzoquinone (Chemical Compound 1) to a 100 mL glass vessel. After 55 mL ethanol was poured into the mixture and dissolved for several minutes at room temperature, the reaction solvent was placed in an ice bath. On some condition, some solids might still remain undissolved in the reaction solvent.

Figure 4A:
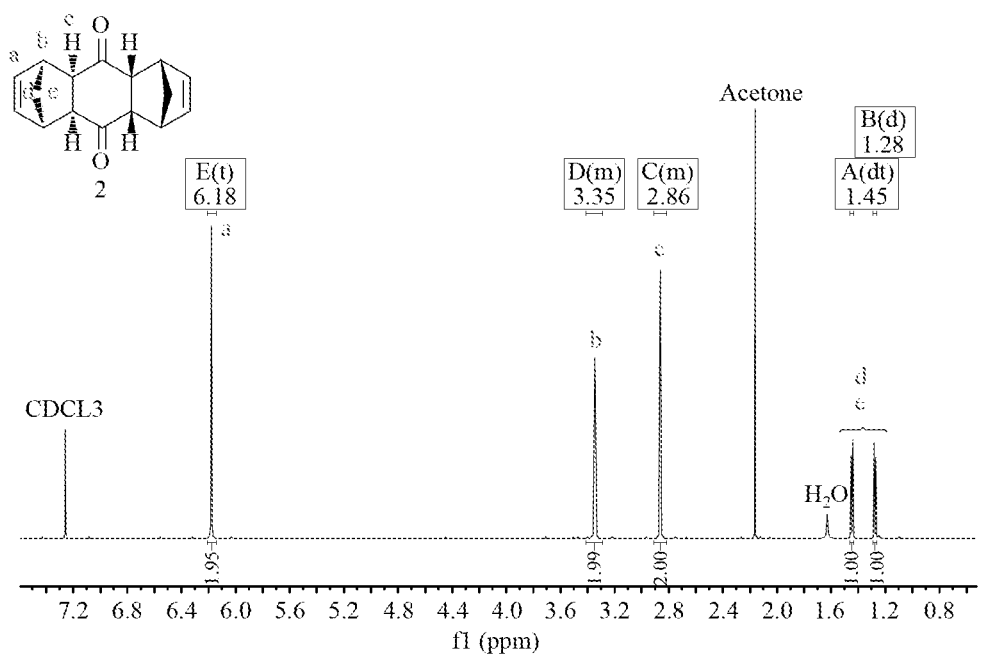
FIG. 4A and FIG. 4B are $^1$H NMR spectrum and EI-mass spectrum of Chemical Compound 2 in accordance with the present invention.
Figure 4B:
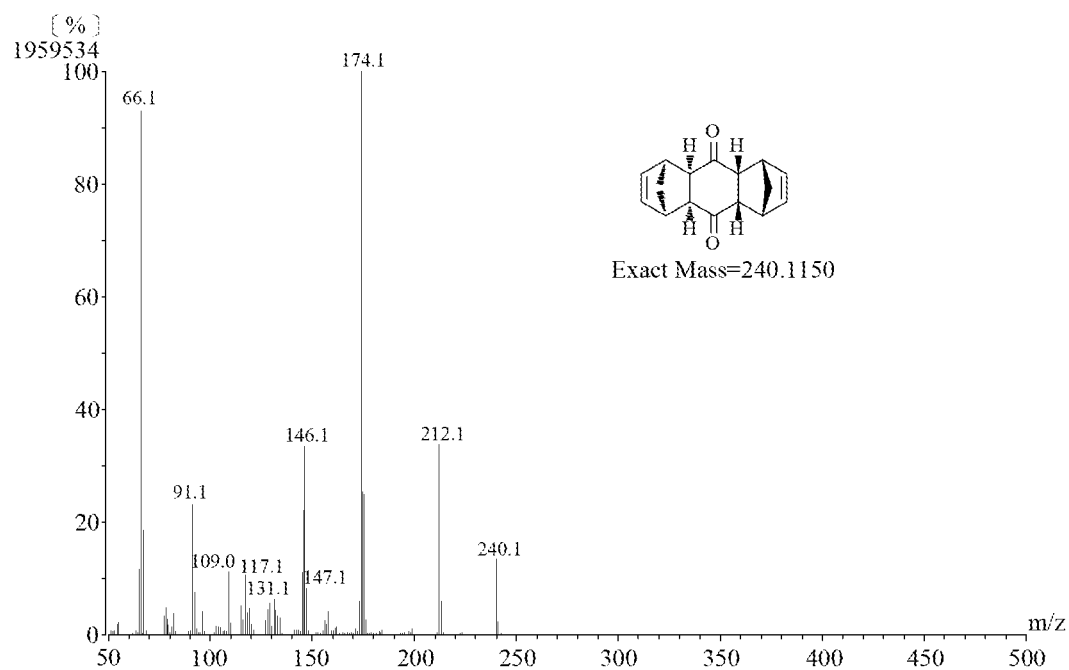

Further a distillation unit containing dicyclopentadiene was used for decomposition into 1,3-cyclopentadiene at 180 to 220° C. 14.7 g (222.04 mmol) 1,3-cyclopentadiene was added to ethanol solution containing 1,4-benzoquinine and stirred in ice bath. The solution gradually turned pale from golden yellow and gradually precipitated into white solid. After the reaction was stirred at 0° C. for 4 hours, the solution was filtered to collect the white solids on the filter cake, and a small amount of iced ethanol was used to wash the solid surface. After drying, 11.2 g of white solid product was obtained, with a yield of 84.2%. The $^1$H NMR spectrum of Chemical Compound 2 are shown in FIG. 4A and the EI-mass spectrum are shown in FIG. 4B.

Chemical Compound 3a (CDE)—(1R,4S,4aS,5S, 8R,8aS,9aR,10aR)-4a,8a-diethyl-1,4,4a,5,8,8a,9a, 10a-° C.tahydro-1,4:5,8-dimethanoanthracene-9,10-dione To obtain chemical compound 3a in this embodiment, the synthesis steps are as following:

8.0 g (33.3 mmol) chemical compound 2 was added to a 500 mL three-necked flask stirred with nitrogen by a magnetic stirrer. Further by using 240 mL tetrahydrofuran to completely dissolved the chemical compound 2, the solution was ice bathed for several minutes. After the temperature was balanced for both inside and outside the reaction vessel, potassium tert-butoxide 18.7 g (166.5 mmol) and bromoethane 18.1 g (166.5 mmol) were added into the reaction solution. After the reaction solution was no longer exothermic, the ice bath was removed and the reaction was conducted at room temperature for 4 hours.

Figure 5A:
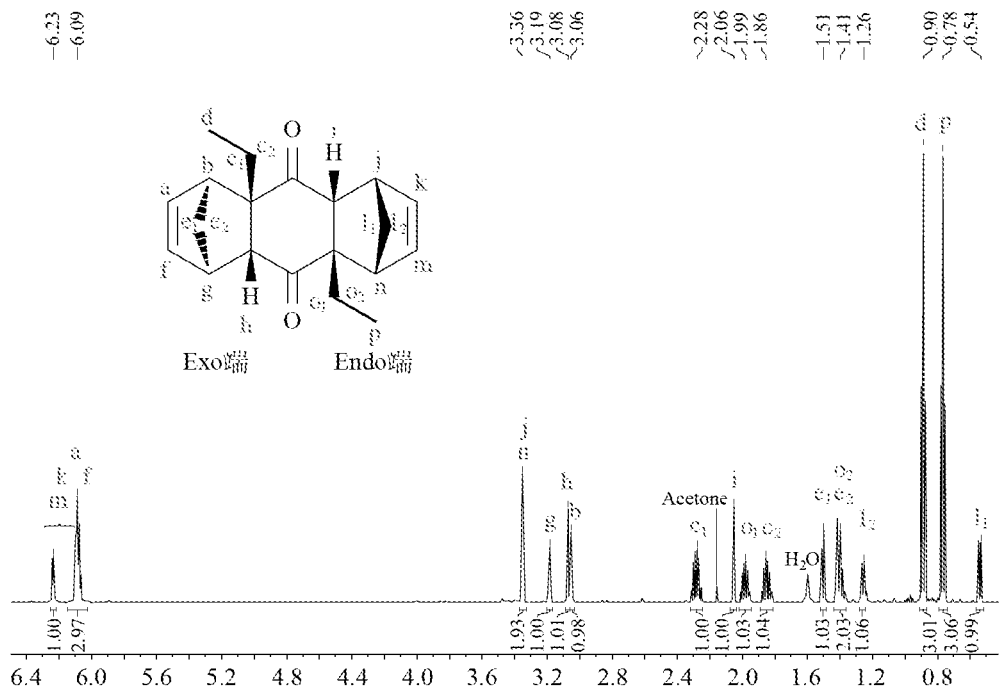
FIG. 5A, FIG. 5B and FIG. 5C are $^1$H NMR spectrum, EI-mass spectrum and XRD of Chemical Compound 3a in accordance with the present invention.
Figure 5B:
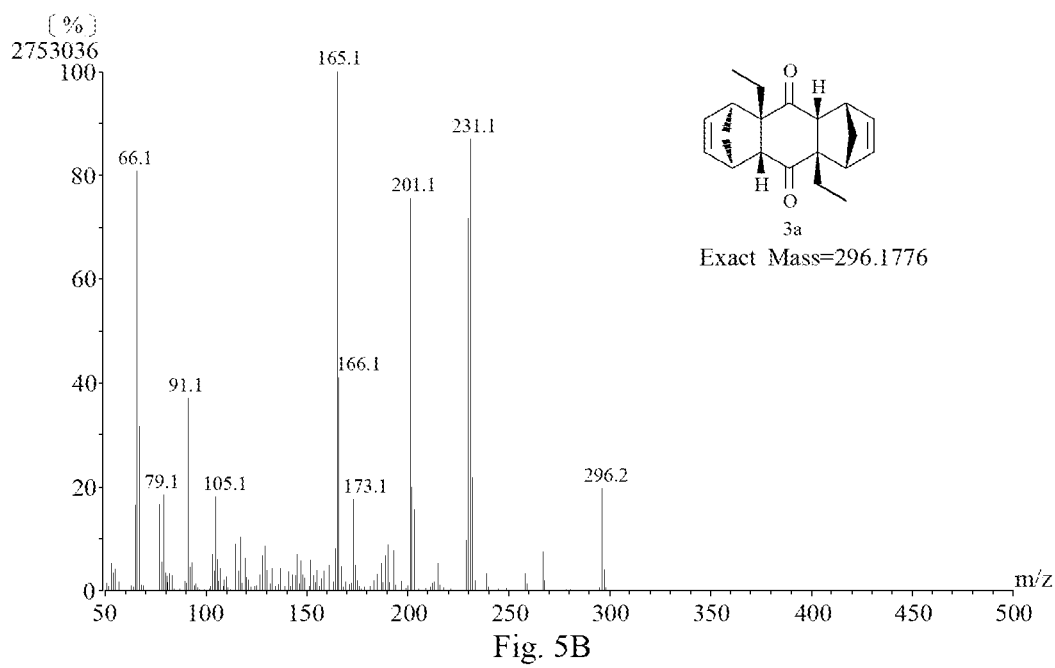
Figure 5C:
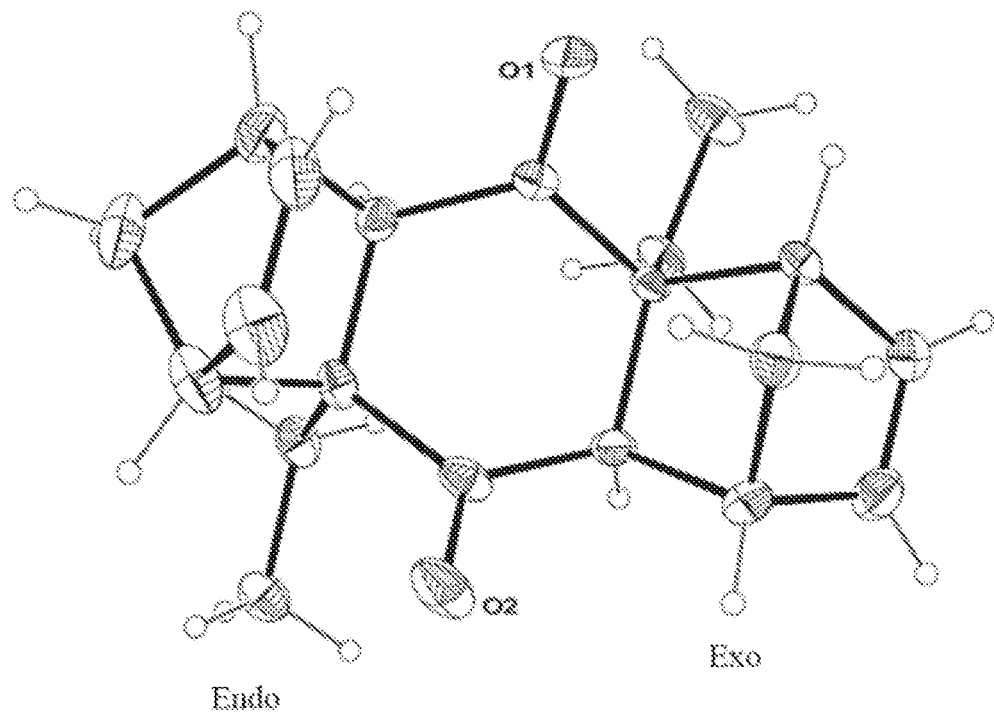

At the end of the reaction, 100 mL of ethyl acetate was added and stirred for several minutes in the flask. The organic layer was extracted with saturated salt water and ethyl acetate, and washed to neutral with saturated salt water to collect the organic solution layer. After removing the solvent by anhydrous magnesium sulfate and reduced pressure and concentrate, the oily paste product was obtained. After adding a little amount of n-hexane (about 4 mL), the solution was remained at room temperature for one night, and transparent crystals gradually grew in the bottle. The solids were filtered and collected, and the solid surface was washed with iced n-hexane to obtain the solid product. The solid was sublimated at 90-120° C. and the upper side of the solid was collected to obtain about 3.5 g of white solid powder with a yield of 35%. The $^1$H NMR spectrum of compound 3a is shown in FIG. 5A, the EI-Mass spectrum is shown in FIG. 5B, and the XRD results are shown in FIG. 5C.

Chemical Compound 4a (CDETE)—(1R,2R,3S,4R, 4aS,5S,6S,7R,8S,8aS,9aR,10aR)-tetramethyl4a,8a-diethyl-9,10-dioxotetradecahydro-1,4:5,8-dimethanoanthracene-2,3,6,7-tetracarboxylate To obtain chemical compound 4a in this embodiment, the synthesis steps are as following:

Add 4.0 g (13.5 mmol) chemical compound 3a to a 250 mL autoclave with nitrogen and stir by magnetic stirrer, and dissolve it completely in 20 mL chloroform. 40 mL anhydrous methanol, 0.204 g (0.194 mmol) 10% Pd/C and 7.48 g (55.6 mmol) copper chloride were added, and the autoclave was locked. Then connect the carbon monoxide cylinder, replace the nitrogen in the autoclave with carbon monoxide, close the vent valve, adjust the pressure to 5 kg/cm$^2$, and stir vigorously at room temperature for 3 days.

After the reaction completed, the carbon monoxide in the autoclave was slowly discharged until the pressure returned to 1 atmosphere. Then, the autoclave was opened and 30 mL chloroform was added into the flask and stirred for 15 minutes. The catalyst was removed by filtration with celite. The filtrate was collected and extracted with saturated salt water and chloroform. The organic layer at lower side of the flask was collected and then washed to neutral with saturated salt water. After dehydrating with anhydrous magnesium sulfate, the chloroform is removed using a vacuum concentration device for obtaining a beige to white solid. The solid was dried and then repeat the same procedures as mentioned above for 3 days to have 6.1 g of brown solid obtained after extraction and drying, with a yield of 85%.

Figure 6A:
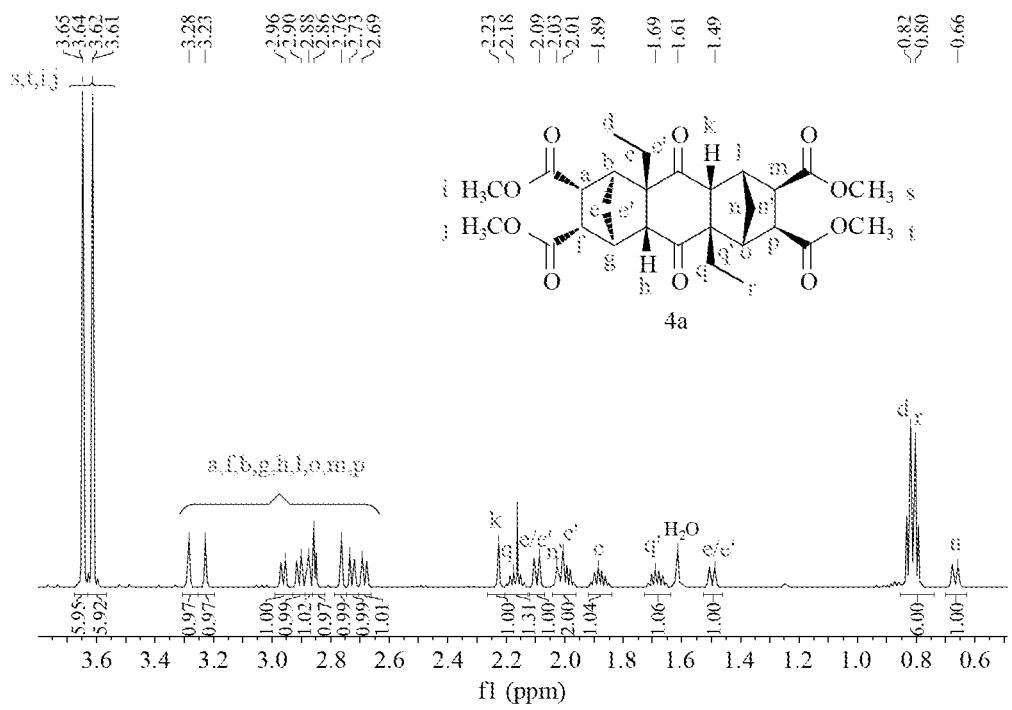
FIG. 6A, FIG. 6B and FIG. 6C are $^1$H NMR spectrum, EI-mass spectrum and XRD of Chemical Compound 4a in accordance with the present invention.
Figure 6B:
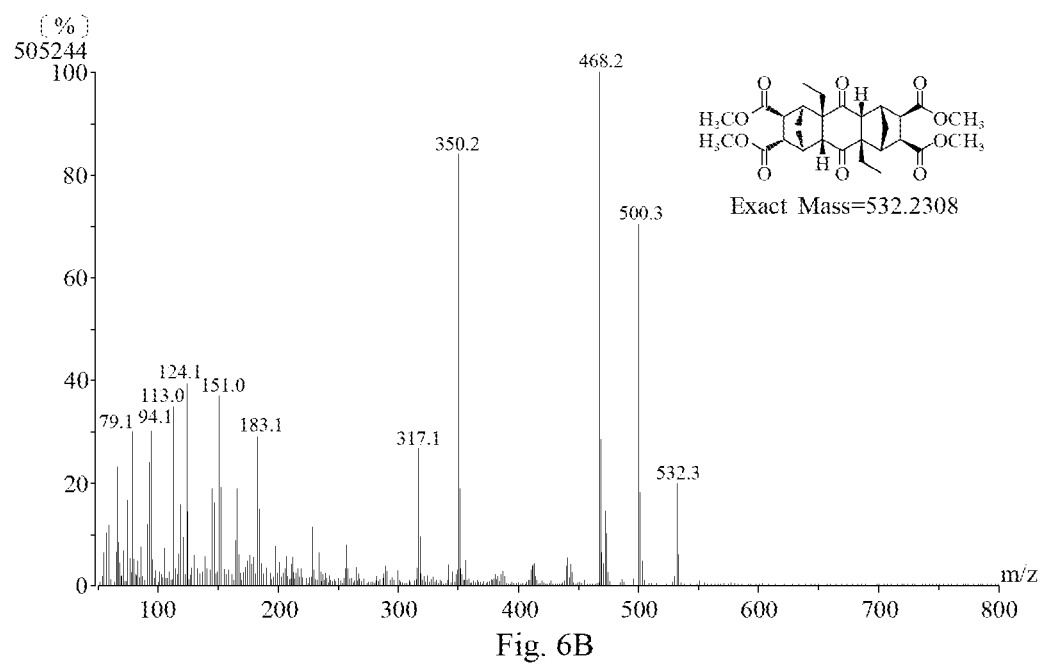
Figure 6C:
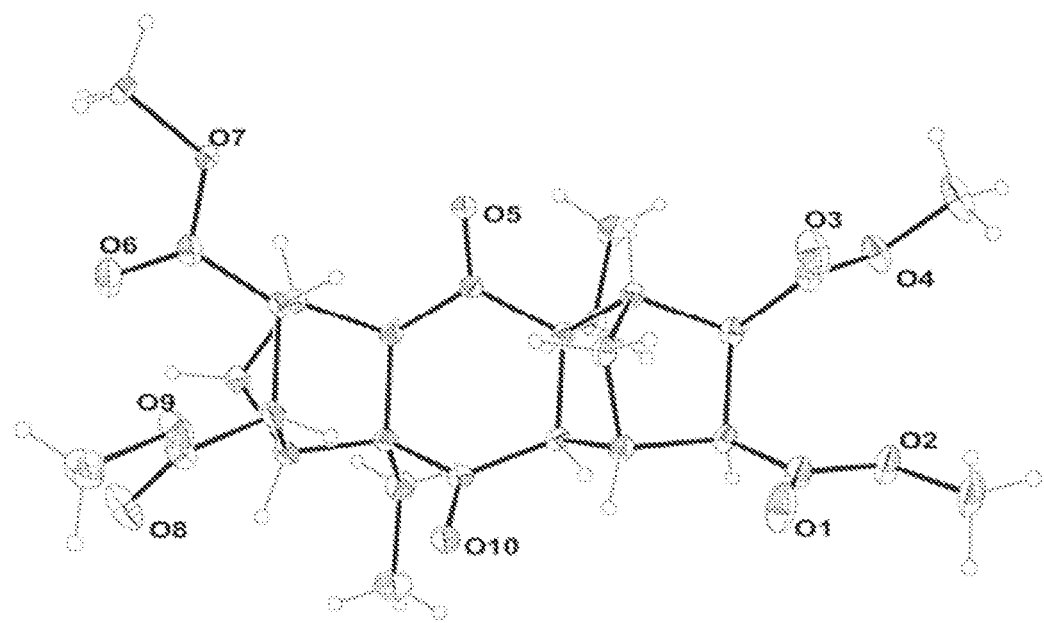

The brown solid was heated with a small amount of acetone (about 5 mL) and boiled for several minutes, then cooled to room temperature and left for several hours. After one night in the refrigerator, the solid was filtered and collected. Surface of the solid was washed with iced acetone and dried to obtain 2.38 g of white solid, with a total yield of 33.2%. The $^1$H NMR spectrum of compound 4a is shown in FIG. 6A, the EI-Mass spectrum in FIG. 6B, and the XRD results in FIG. 6C.

Figure 7A:
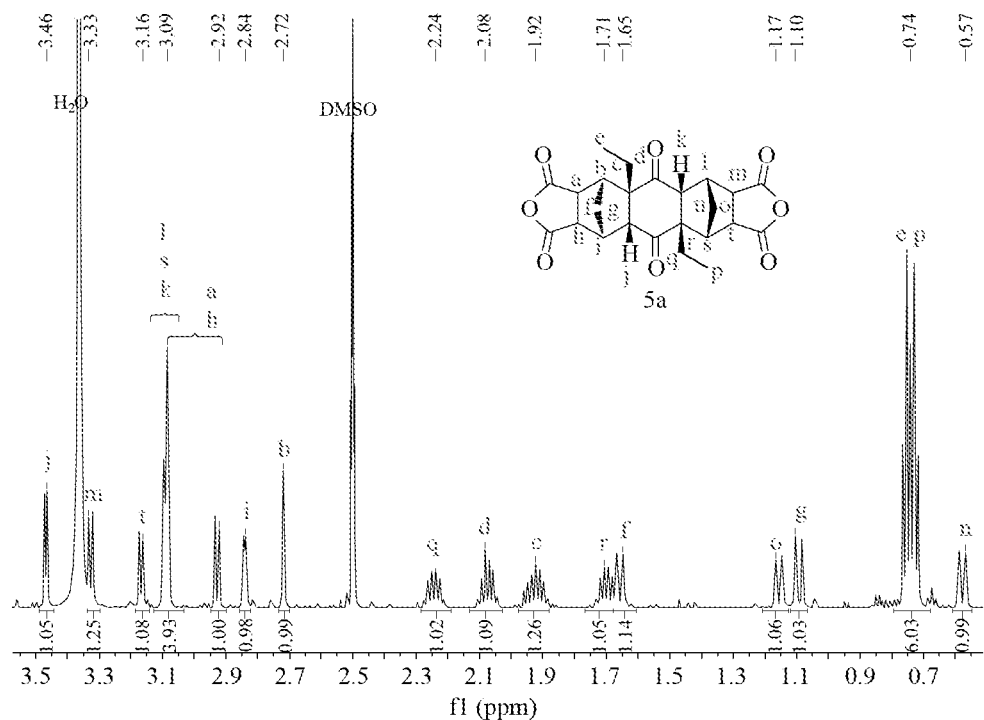
FIG. 7A and FIG. 7B are $^1$H NMR spectrum and EI-mass spectrum of Chemical Compound 5a in accordance with the present invention.
Figure 7B:
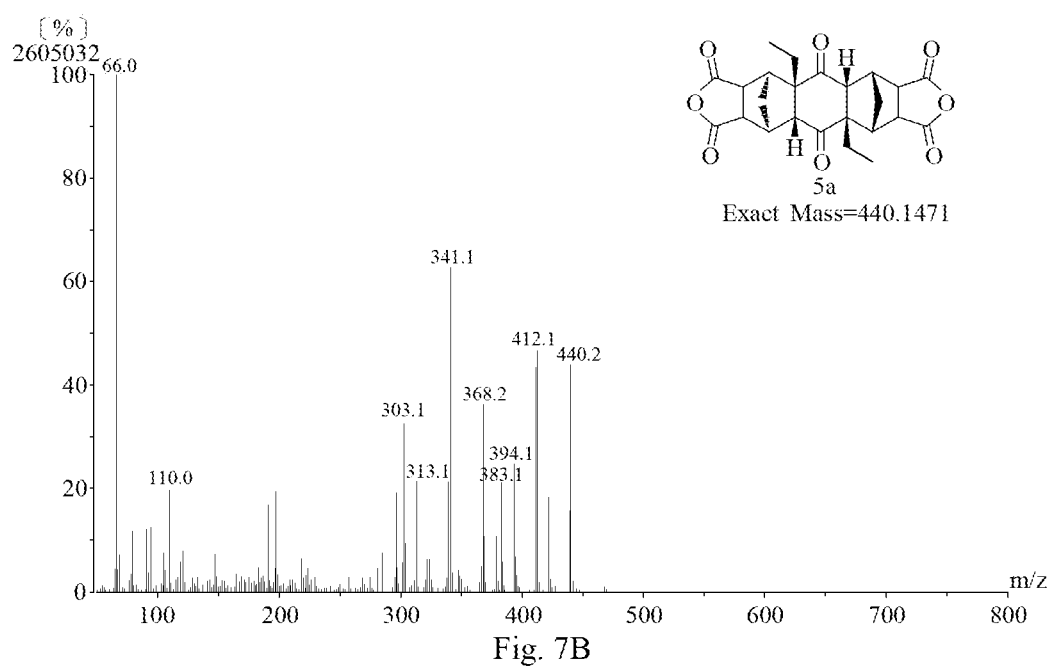

Chemical Compound 5a (CDEDA)—(1R,2R,3S,4R, 4aS,5S,6S,7R,8S,8aS,9aR,10aR)-tetramethyl 4a,8a-diethyl-9,10-dioxo tetradecahydro-1,4:5,8-dimethanoanthracene-2,3,6,7-tetracarboxylic dianhydride To obtain chemical compound 5a in this embodiment, the synthesis steps are as following:

Add 1.0 g (1.88 mmol) of chemical compound 4a and 19 mL acetic acid to a 25 mL three-necked flask and stir for several minutes, followed by 0.1 g (0.67 mmol) trifluoromethylsulfonic acid and nitrogen. After the temperature is raised to 130° C., making the solution reflux for half an hour. The condenser tube is replaced by a distillation tube with a dosing tube connected to the other end. The dosing rate is adjusted to make the dripping rate of the acetic acid equal to the distillation rate. After distillation for 4 hours, the dosing tube is removed and the solvent is steamed. Finally, the solvent was completely drained by means of decompression to obtain 0.98 g of brown solid. Boil the solid product with about 70 mL of toluene after filtering. The product was remained at room temperature for 5 hours and moved to the refrigerator for overnight. Pure the solution into a large amount of n-hexane making the white solid to be precipitated at the bottom, then collected by centrifuge and filter for obtaining white solid. After heating in vacuum oven for drying, white solid product was obtained 0.27 g with 32.7% total yield. The $^1$H NMR spectrum of chemical compound 5a are shown in FIG. 7A and the EI-mass spectrum are shown in FIG. 7B.

Figure 8A:
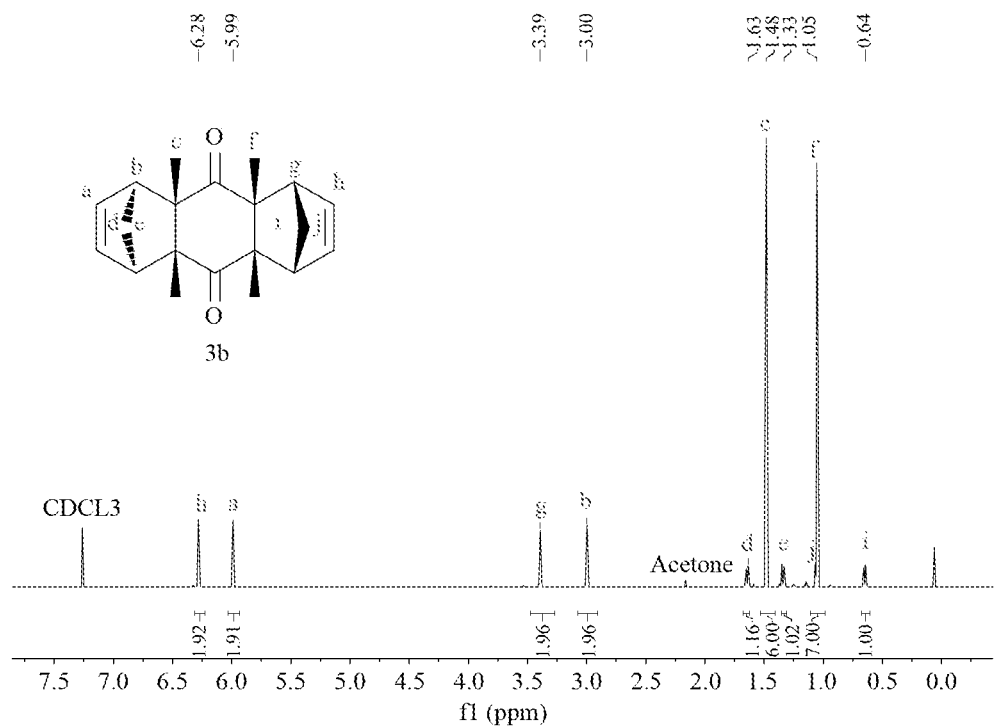
FIG. 8A, FIG. 8B and FIG. 8C are $^1$H NMR spectrum, EI-mass spectrum and XRD of Chemical Compound 3b in accordance with the present invention.
Figure 8B:
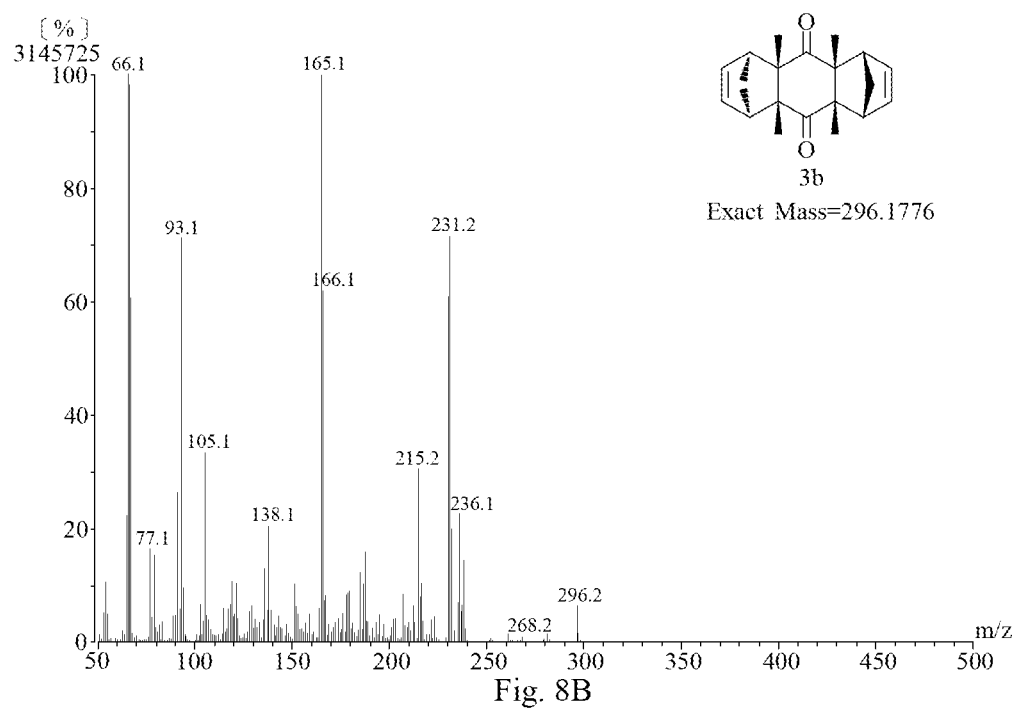
Figure 8C:
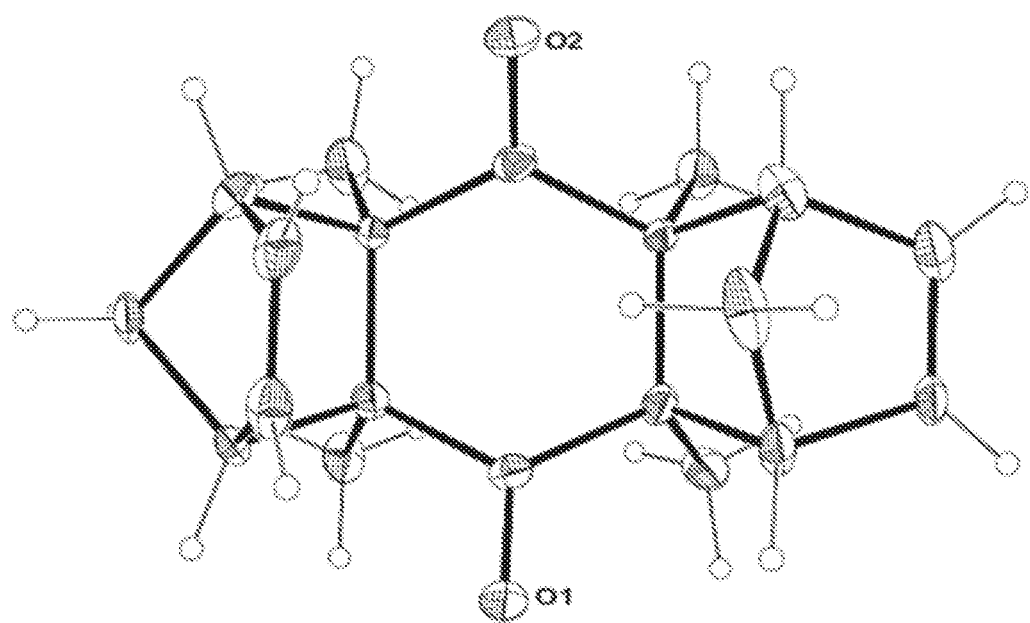

Chemical Compound 3b (CTM)—(1R,4S,4aR,5S, 8R,8aR,9aS,10aS)-4a,8a,9a,10a-tetramethyl-1,4,4a, 5,8,8a,9a,10a-octahydro-1,4:5,8-dimethanoanthracene-9,10-dione To obtain chemical compound 3b in this embodiment, the synthesis steps are as following:

8.0 g (33.3 mmol) chemical compound 2 was added to a 500 mL three-necked flask stirred with nitrogen by magnetic stirrer. After the solution was completely dissolved in 200 mL tetrahydrofuran, the solution was ice bathed for several minutes. After reaching temperature balanced of the flask, 18.7 g of potassium tert-butoxide (166.5 mmol) and 33.1 g of iodomethane (233.1 mmol) were added into the solution. After stirring in the ice bath for another 10 minutes, the ice bath was removed with further react at room temperature for 24 hours. After the reaction, adequate ethyl acetate was added and stirred in the flask for several minutes, followed by extraction with saturated salt water and ethyl acetate. After the reaction, add some ethyl acetate and stir for several minutes in the flask. Then, the organic solution layer was extracted with saturated salt water and ethyl acetate, and was washed to neutral with saturated salt water. Then, anhydrous magnesium sulfate was added to remove the water. After filtered and concentrated to remove the solvent, a golden oil paste product was obtained. A little n-hexane was added, and the solution was left at room temperature for 3 hours and then stay in a freezer for overnight. Transparent crystals gradually grew in the flash. The solids were filtered and collected, and the surface of the solids was rinsed with iced n-hexane to obtain white solids. The solid was sublimated at 90-120° C. and the upper solid was collected to obtain about 6.0 g white solid powder with a total yield of 61%. The $^1$H NMR spectrum of compound 3b is shown in FIG. 8A, the EI-Mass spectrum in FIG. 8B and the XRD results in FIG. 8C.

Figure 9:
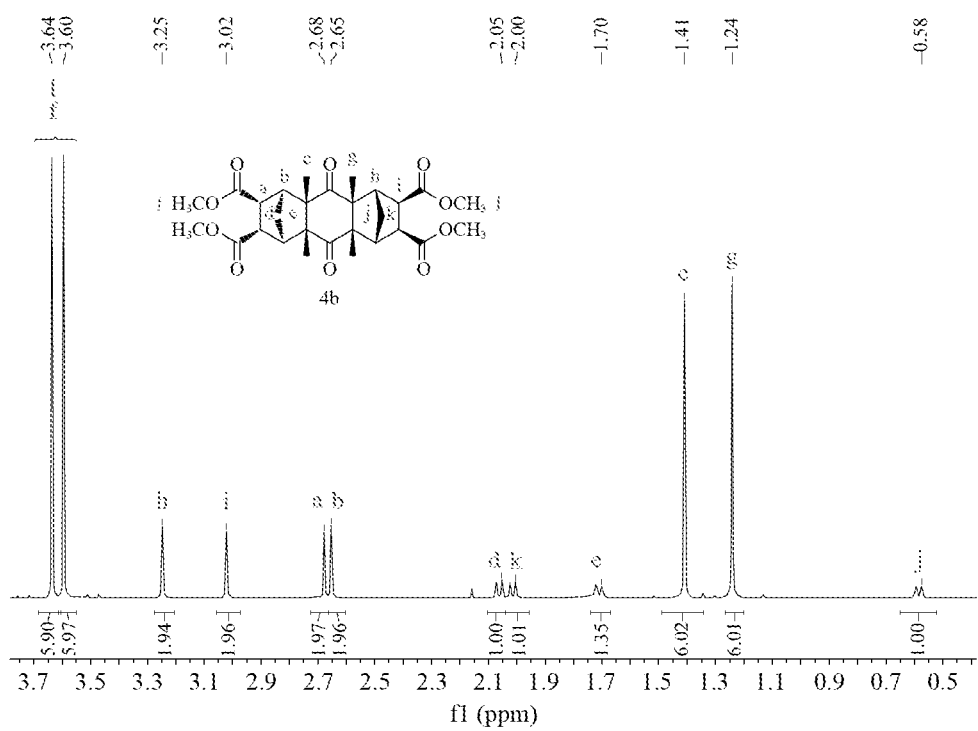
FIG. 9 is $^1$H NMR spectrum of Chemical Compound 4b in accordance with the present invention.

Chemical Compound 4b (CTMTE)—(1R,2S,3R,4S, 4aR,5S,6R,7S,8R,8aR,9aS,10aS)-tetramethyl 4a,8a, 9a,10a-tetramethyl-9,10-dioxotetradecahydro-1,4:5, 8-dimethanoanthracene-2,3,6,7-tetracarboxylate To obtain chemical compound 4b in this embodiment, the synthesis steps are as following:

4.0 g (13.5 mmol) of chemical compound 3b was added to a 250 mL autoclave stirred with nitrogen by magnetic stirrer. After the solution was completely dissolved in 10 mL chloroform, 40 mL anhydrous methanol, 0.204 g (0.194 mmol) 10% Pd/C and 7.48 g (55.6 mmol) copper chloride were added, and the autoclave was locked. Connecting the autoclave with a carbon monoxide cylinder. And replace the nitrogen in the autoclave with carbon monoxide and close the vent valve. Adjusting the pressure to 5 kg/cm$^2$, and stir vigorously at room temperature for 3 days. After the reaction, the carbon monoxide in the autoclave was slowly discharged until the pressure returned to 1 atmosphere. Then the autoclave was opened and 0.204 g (0.194 mmol) 10% Pd/C and 7.48 g (55.6 mmol) copper chloride were added again. 5 kg/cm$^2$ of carbon monoxide was added for further reaction for 3 days. The $^1$H NMR spectrum of compound 4b is shown in FIG. 9.

After the reaction, the carbon monoxide in the autoclave is slowly vented until the pressure returns to 1 atmosphere. The catalyst was removed with filtration by celite. The filtrate was collected and extracted with saturated salt water and chloroform. The organic layer was collected and then washed to neutral with saturated salt water. After dehydrating with anhydrous magnesium sulfate, chloroform was removed by vacuum concentration device, and 6.1 g of light yellow solid was obtained with a yield of 85%.

The yellow solid was heated with a small amount of acetone (about 5 mL) and boiled for several minutes, then cooled to room temperature and stayed for several hours. After remaining in the refrigerator for overnight, the solid was filtered and collected. Surface of the solid was washed with ice acetone and dried to obtain 4.3 g of white solid with a total yield of about 60%.

Figure 10A:
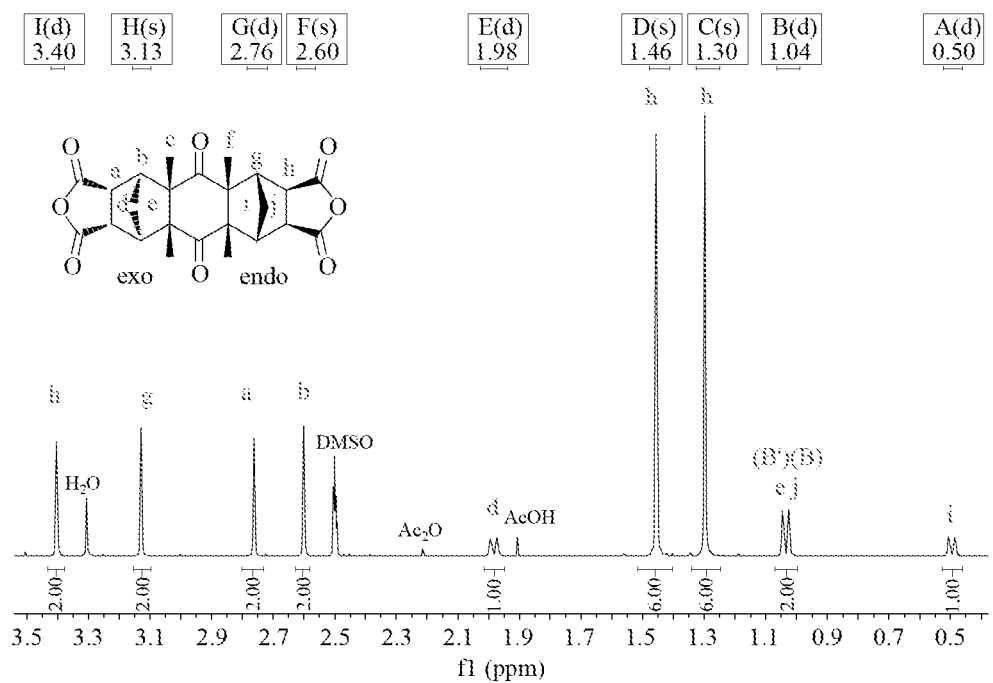
FIG. 10A, FIG. 10B and FIG. 10C are $^1$H NMR spectrum, EI-mass spectrum and XRD of Chemical Compound 5b in accordance with the present invention.
Figure 10B:
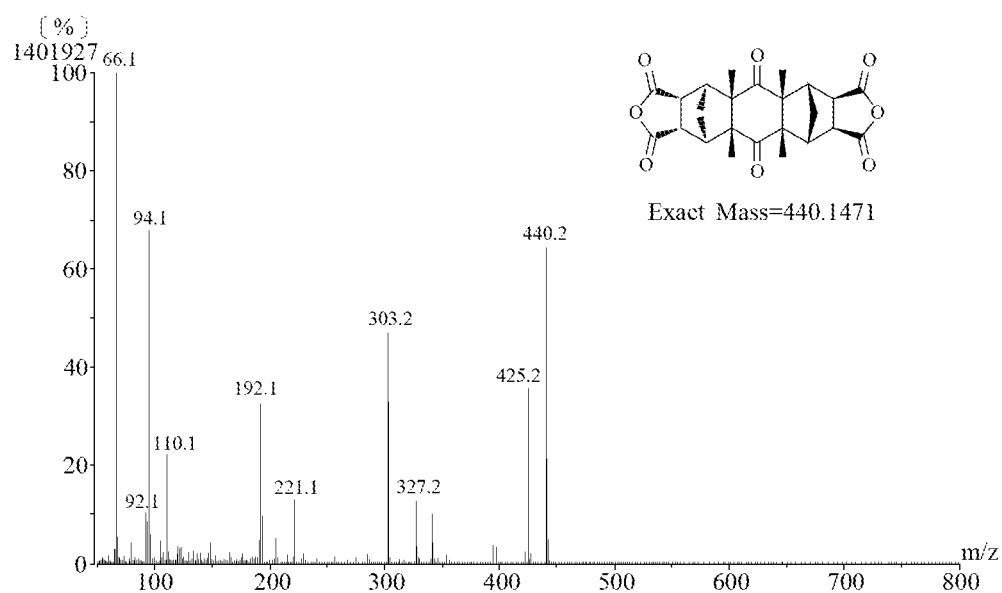
Figure 10C:
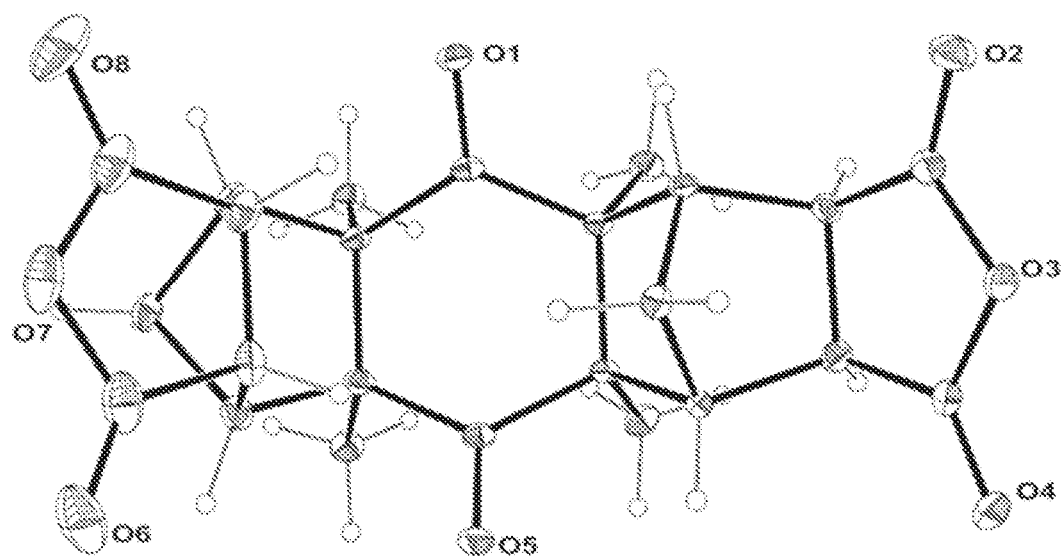

Chemical Compound 5b (CTMDA)—(1R,2S,3R,4S, 4aR,5S,6R,7S,8R,8aR,9aS,10aS)-tetramethyl 4a,8a, 9a,10a-tetramethyl-9,10-dioxotetradecahydro-1,4:5, 8-dimethanoanthracene-2,3,6,7-tetracarboxylic dianhydride To obtain chemical compound 5b in this embodiment, the synthesis steps are as following:

Add 1.0 g (1.88 mmol) chemical compound 4b and 19 mL acetic acid to a 25 mL three-necked flask with a condenser tube and a magnetic stirrer. After stirring for several minutes, 0.1 g (0.67 mmol) trifluoromethylsulfonic acid was added, and further applied with nitrogen. After raising the temperature to 130° C. for half an hour to reflux the solution, the temperature is raised to 150° C. for further reflux for 4 hours. The condenser tube is replaced by a distillation tube and condensed water is added. The solution is distilled until there is no longer a solvent dripping to have a thick concentrated solution in the flash. Remove the distillation device and the oil pan, make temperature of the solution naturally decrease to room temperature. Extracting and filtering the solution to collect the white solids. Wash the surface of the solids with acetic acid, and then wash the surface with diethyl ether, and collect the white solids on the filter cake. After drying in a vacuum oven at 130° C., 0.70 g of white solid was obtained, and the yield of product was 85%. 1.53 g of white solid was recrystallized with 50 mL acetic anhydride to obtain 0.72 g of colorless transparent crystal. The $^1$H NMR spectrum of compound 5b is shown in FIG. 10A, the EI-Mass spectrum in FIG. 10B and the XRD results in FIG. 10C.

Chemical Compound 3c (CDM)—(1R,4S,4aR,5S, 8R,8aS,9aS,10aR)-4a,8a-dimethyl-1,4,4a,5,8,8a,9a, 10a-° C.tahydro-1,4:5,8-dimethanoanthracene-9,10-dione To obtain chemical compound 3c in this embodiment, the synthesis steps are as following:

Add 8.0 g (33.3 mmol) of chemical compound 2 to a 500 mL three-necked flask stirred with nitrogen by a magnetic stirrer. After the solution was completely dissolved in 200 mL tetrahydrofuran, the solution was ice bathed for several minutes until the temperature reached balance. The potassium tert-butoxide 18.7 g (166.5 mmol) and iodomethane 23.6 g (166.5 mmol) were added into the solution. After stirring in the ice bath for 10 minutes, the ice bath was removed and the solution was left at room temperature for 4 hours.

Figure 11A:
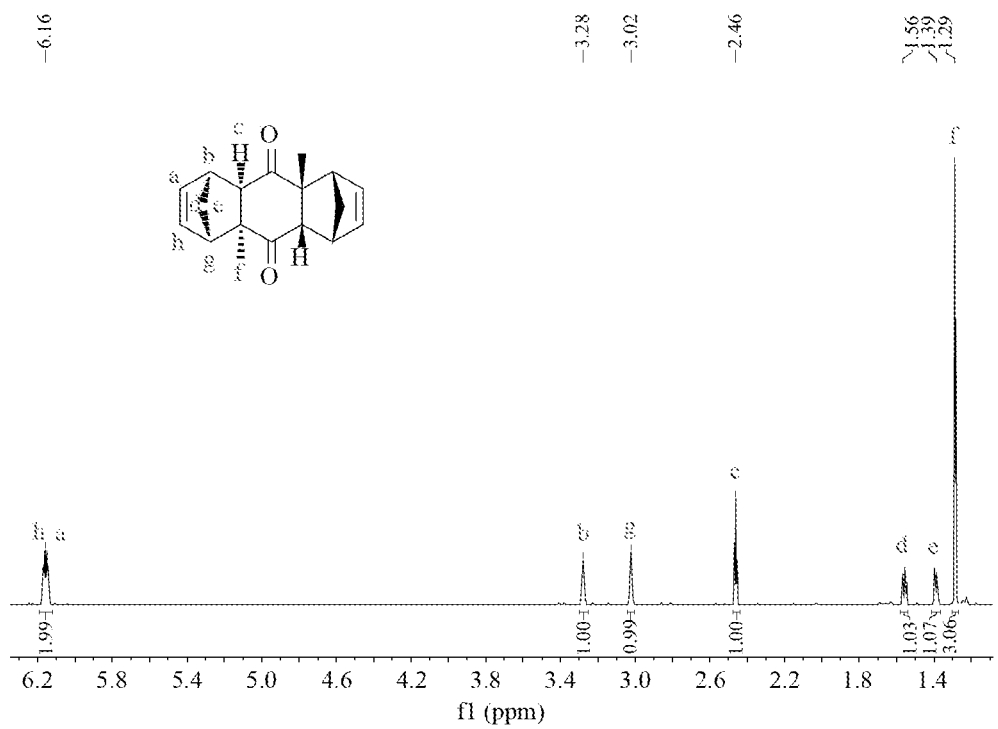
FIG. 11A, FIG. 11B and FIG. 11C are $^1$H NMR spectrum, EI-mass spectrum and XRD of Chemical Compound 3c in accordance with the present invention.
Figure 11B:
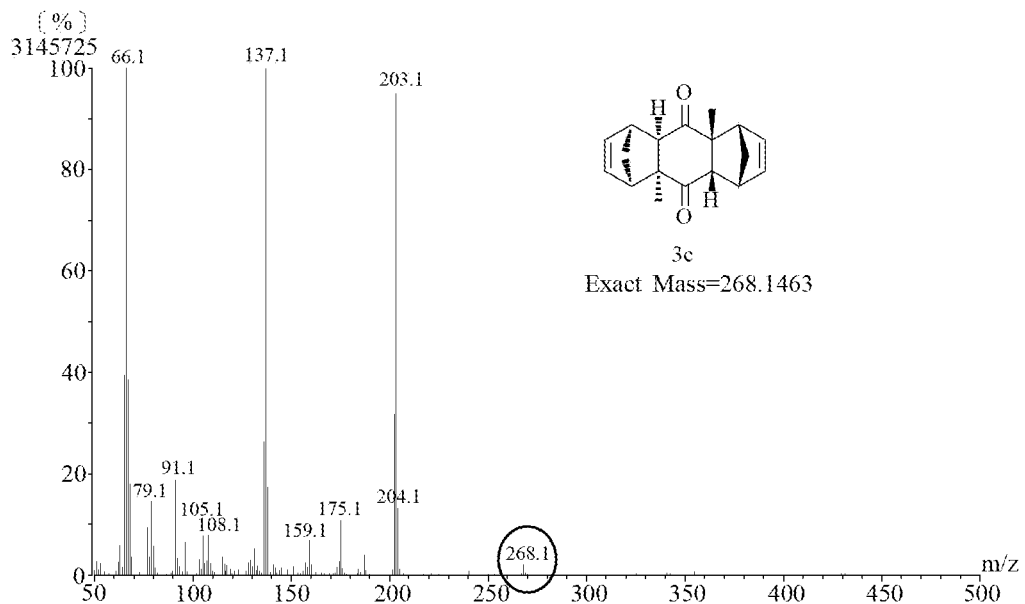
Figure 11C:
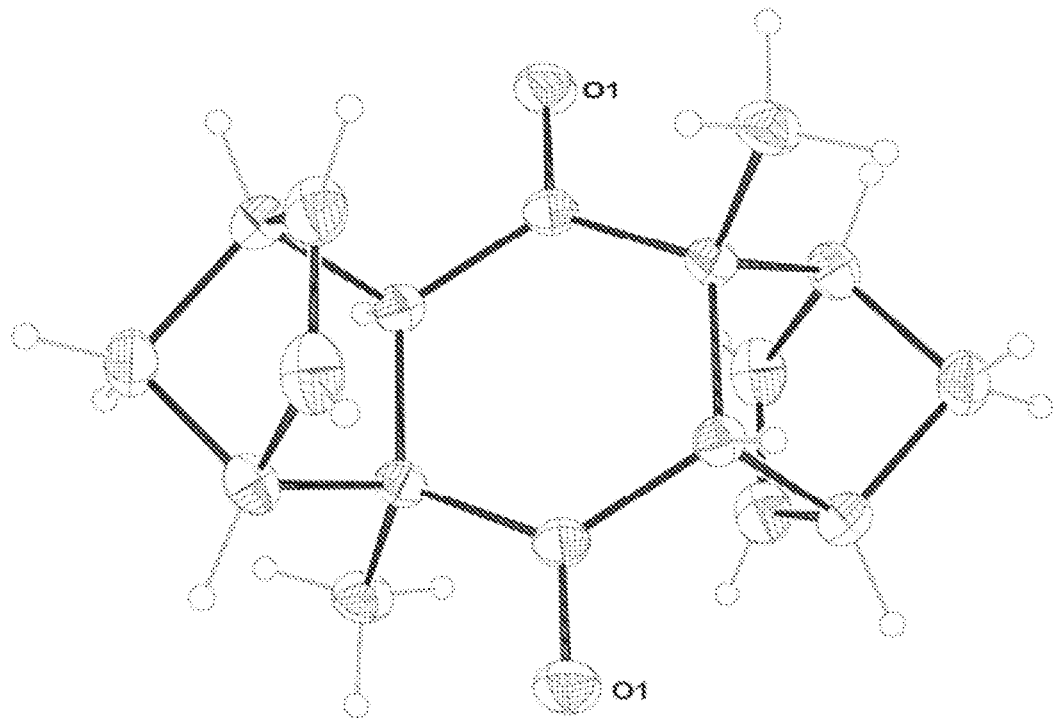

After the reaction, add adequate ethyl acetate and stir for several minutes in the three-necked flask. Then the organic solution was extracted with saturated salt water and ethyl acetate further washed to neutral with saturated salt water. Then add anhydrous magnesium sulfate to remove water. Extract and filter the solution in the aspirator bottle, and remove the solvent by vacuum concentration. As the amount of the solvent decreased, colorless crystals were gradually precipitated in the flask. When the solvent in the flask appeared to be an oily paste, the reduced pressure concentration was stopped, and the solid was collected by extraction and filtration. Surface of the solid surface was washed with ethyl acetate at 0° C. The solid on the filter cake was removed and dried under vacuum at a temperature below 60° C. to obtain 1.8 g white granular crystals with a yield of 20%. The $^1$H NMR spectrum of compound 3c is shown in FIG. 11A, the EI-Mass spectrum is shown in FIG. 11B, and the XRD results are shown in FIG. 11C.

Figure 12A:
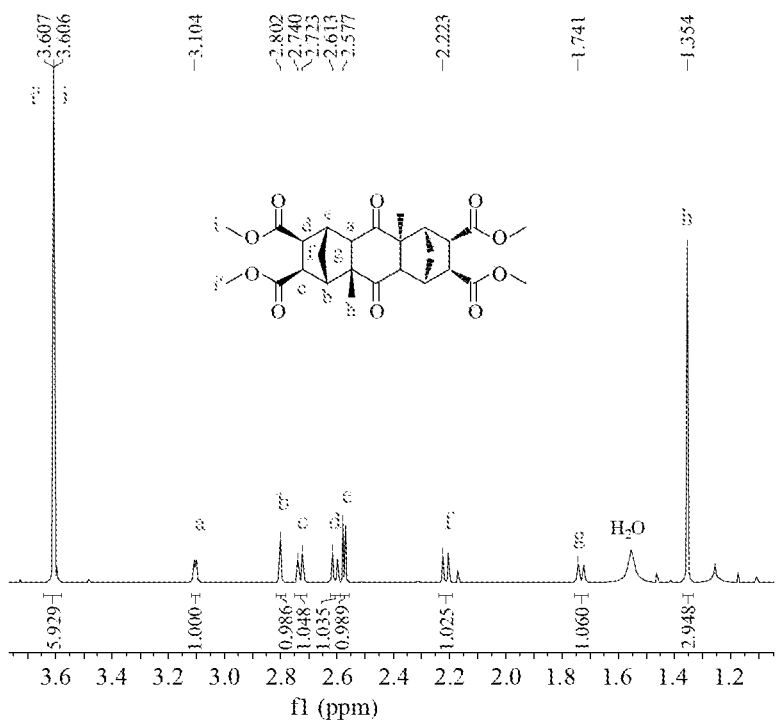
FIG. 12A and FIG. 12B are $^1$H NMR spectrum and EI-mass spectrum of Chemical Compound 4c in accordance with the present invention.
Figure 12B:
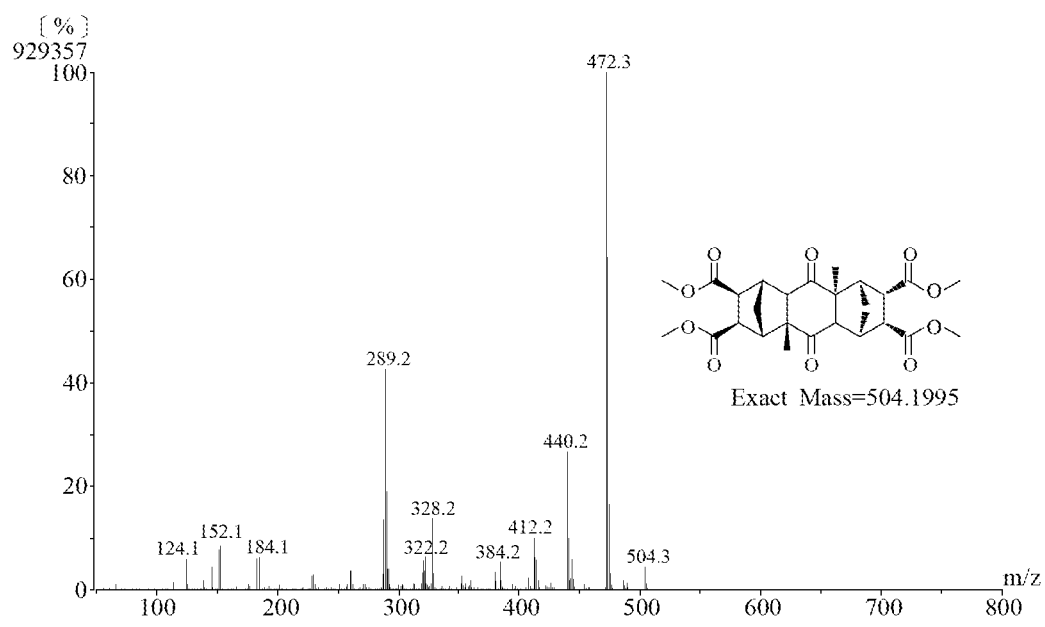

Chemical Compound 4c (CDMTE)—(1R,2R,3S,4R, 4aS,5S,6S,7R,8S,8aR)-tetramethyl 4a,8a-dimethyl-9,10-dioxotetradecahydro-1,4:5,8-dimethanoanthracene-2,3,6,7-tetracarboxylate To obtain chemical compound 4c in this embodiment, the synthesis steps are as following:

2.5026 g (9.3 mmol) of chemical compound 4a was added to a 250 mL autoclave stirred with nitrogen by magnetic stirrer. After the solution was completely dissolved in 10 mL chloroform, 28 mL anhydrous methanol, 0.115 g (0.109 mmol) 10% Pd/C and 5.0254 g (37.4 mmol) copper chloride were added, and the autoclave was locked. Then connect the autoclave with a carbon monoxide cylinder, replace the nitrogen in the autoclave with carbon monoxide, close the vent valve, adjust the pressure to 5 kg/cm$^2$, and stir vigorously at room temperature for 3 days. After the reaction, the carbon monoxide in the autoclave was slowly discharged until the pressure returned to 1 atmosphere and no more gas was discharged. Then the autoclave was opened and 0.115 g (0.109 mmol) 10% Pd/C and 5.0254 g (37.4 mmol) copper chloride were added again. 5 kg/cm$^2$ of carbon monoxide was added for further reaction by 3 days. The $^1$H NMR spectrum of compound 4c are shown in FIG. 12A and EI-Mass spectrum in FIG. 12B.

After the reaction, the carbon monoxide in the autoclave is slowly discharged until the pressure returns to 1 atmosphere. The catalyst was removed with filtration by celite. The filtrate was collected and extracted with saturated salt water and chloroform. The organic layer was collected and then washed to neutral with saturated salt water. After dehydrating with anhydrous magnesium sulfate, the chloroform was removed by vacuum concentration to obtain a light yellow solid of 3.3168 g with a yield of 70%.

Chemical Compound 5c (CDMDA)—(3 aR,4S,4aR, 6R,6aR,9aS,10R,10aS, 12S,12aS)-4a,10a-dimethyl° C.tahydro-4,12:6,10-dimethanoanthra[2,3-c:6,7-c'] difuran-1,3,5,7,9,11(3aH,5aH,9aH,11aH)-hexaone To obtain chemical compound 5c in this embodiment, the synthesis steps are as following:

Adding 0.9310 g (1.84 mmol) chemical compound 4c and 18.5 mL acetic acid to a 25 mL three-necked flask with a condenser tube and a magnetic stirrer for stirring for several minutes, followed by adding 1.5 g (10.05 mmol) trifluoromethylsulfonic acid with fluxing nitrogen. The temperature was raised to 130° C. for half an hour, and then the temperature was raised to 150° C. for another 4 hours. After the reaction, grey precipitation were gradually precipitated in the solution. The oil pan was removed to allow the reaction to naturally reach to the room temperature. The gray-white solids were collected by suction filtration and washed with ice ether. The gray-white solids on the filter cake were collected. The gray-white solids were dried in a vacuum oven at 130° C., and 0.7078 g of gray-white solids were obtained after drying with yield 93%.

Figure 13A:
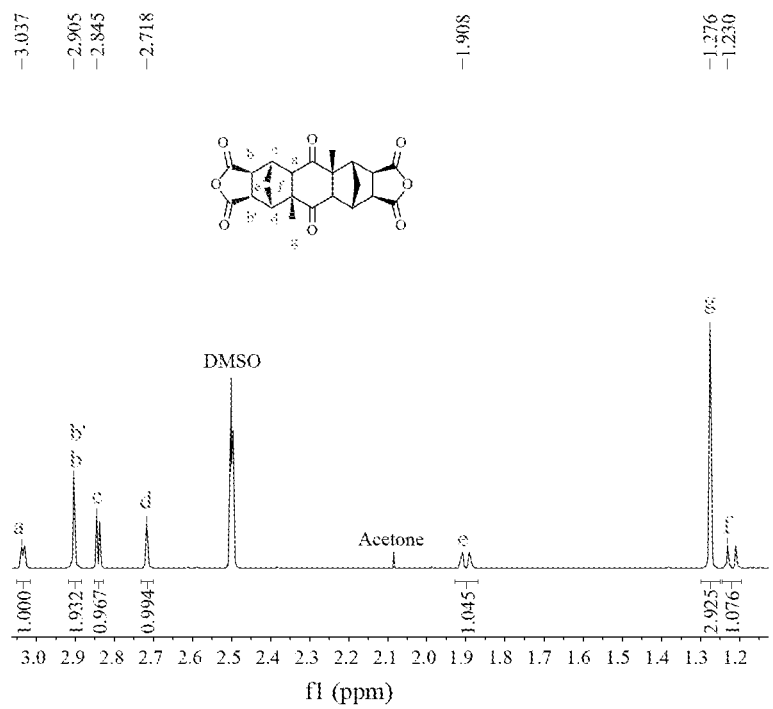
FIG. 13A, FIG. 13B, and FIG. 13C are $^1$H NMR spectrum, EI-mass spectrum and XRD of Chemical Compound 5c in accordance with the present invention.
Figure 13B:
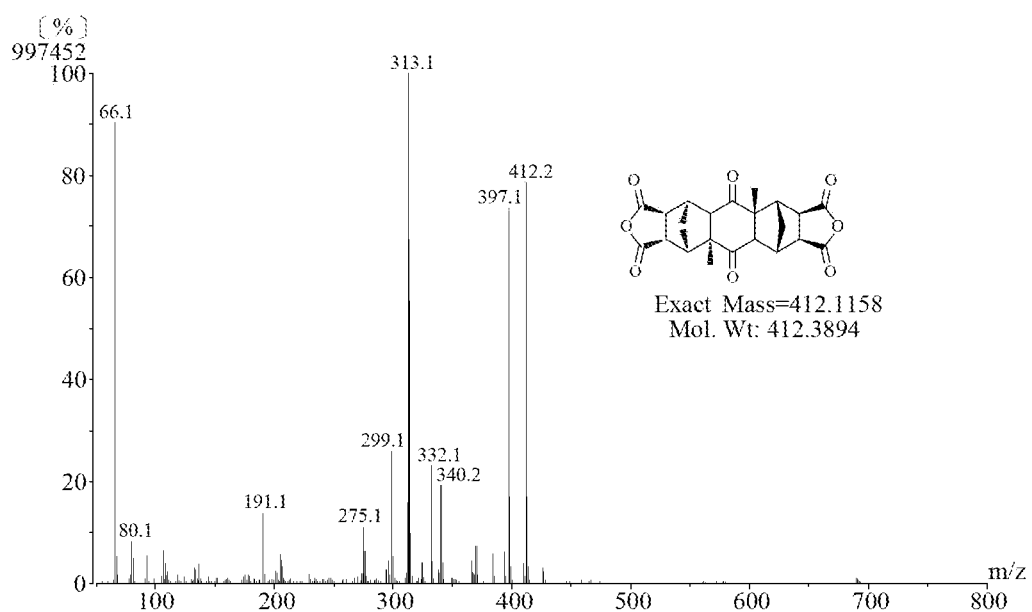
Figure 13C:
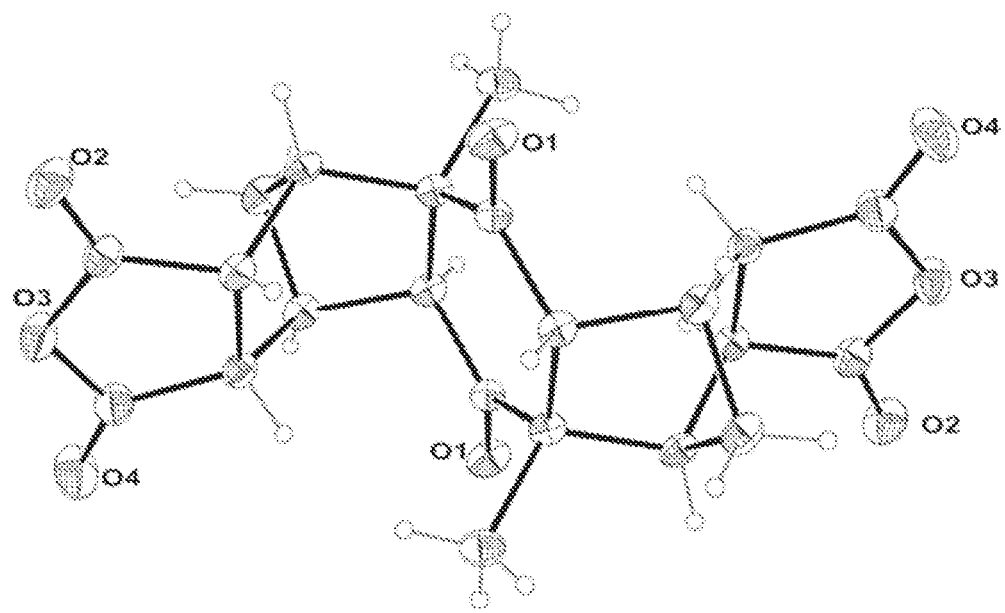

Add 0.7078 g of grayish solid into a 50 ml flask and flux with nitrogen. Add 30 mL of acetic anhydride and heat it up to reflux and stir it vigorously for 5 hours. The white solid was filtered after the temperature was below the room temperature. After the solid surface was cleaned with ice ether, the white solid on the filter cake was collected. After drying in a vacuum oven at 60° C., 0.6974 g of white solid was obtained, and the yield of the product was 91.6%. The $^1$H NMR spectrum of compound 5c is shown in FIG. 13a, the EI-Mass spectrum in FIG. 13b, and the XRD results in FIG. 13c.

A better embodiment of dianhydride monomer of compounds 5a, 5b and 5c is provided with the general structural formula as in Formula (4) above. In addition, the three-dimensional structure of exo-exo-syn-endo-exo or exo-endo-anti-endo-exo are presented in Formula (4) above. In these better embodiments, R1-R4 is a hydrogen atom or a methyl or an ethyl group and has stereoisomerism in the functional group position of R1-R4 as shown in Formulas (5) and (6).

The present invention further conducts a series of testing on the alicyclic dianhydrides from chemical compounds 5a, 5b and 5c. The testing below is mainly compared with the thermal properties of the semi-aromatic PI synthesized by conventional dianhydride monomer. With reference to Chart 1 below, the PI polymer provided in the present invention has a good performance in CTE, Tg, and Td$_{5\%}$. Meanwhile, in the embodiment of PI synthesized from ketone-containing alicyclic dianhydrides, the Tg increases from 354° C. to 460° C. Compare with PI derived from anhydride with similar structure, Td$_{5\%}$ increased from 422° C. to 470° C. CTE is also lower than common monocyclic anhydride. This indicates that the new dianhydride structure provided in the present invention also has a good performance on the thermal dimensional stability of the polymer when it is introduced into the polyimide under the same conditions.

CHART 1

| Polymer | CTE | Tg (° C.) | $Td_{5\%}$ (° C.) | Transparency |
|---|---|---|---|---|
| Present invention PI (CDEDA-ODA) (5a-a) | 42.4 | >270 | 415.5 | High |
| Present invention PI (CTMDA-ODA) (5b-a) | 38.8 | 460 | 470.0 | High |
| Present invention PI (CDMDA-ODA) (5c-a) | 25.7 | 423 | 440.5 | High |
| Compared sample PI (CpODA-ODA) | 49 | 354 | 468 | Low |
| Compared sample PI (DMADA-ODA) | 38 | 379 | 422 | Low |
| Compared sample PI $(DNDA_{(xx)}$-ODA) | 49 | 439 | 502 | Low |
| Compared sample PI $(DNDA_{(xn)}$-ODA) | 66 | 441 | 502 | Low |
| Compared sample PI $(BHDA_{(xn)}$-ODA) | 53.5 | 425 | 516 | Low |
| Compared sample PI $(BODA_{(xn)}$-ODA) | — | 383 | 464 | Low |
| Compared sample PI (CBDA-ODA) | 50.3 | 364 | 452 | Low |
| Compared sample PI $(HPMD_{(xxxx)}$-ODA) | 56 | 333 | 442 | Low |

Figure 2:
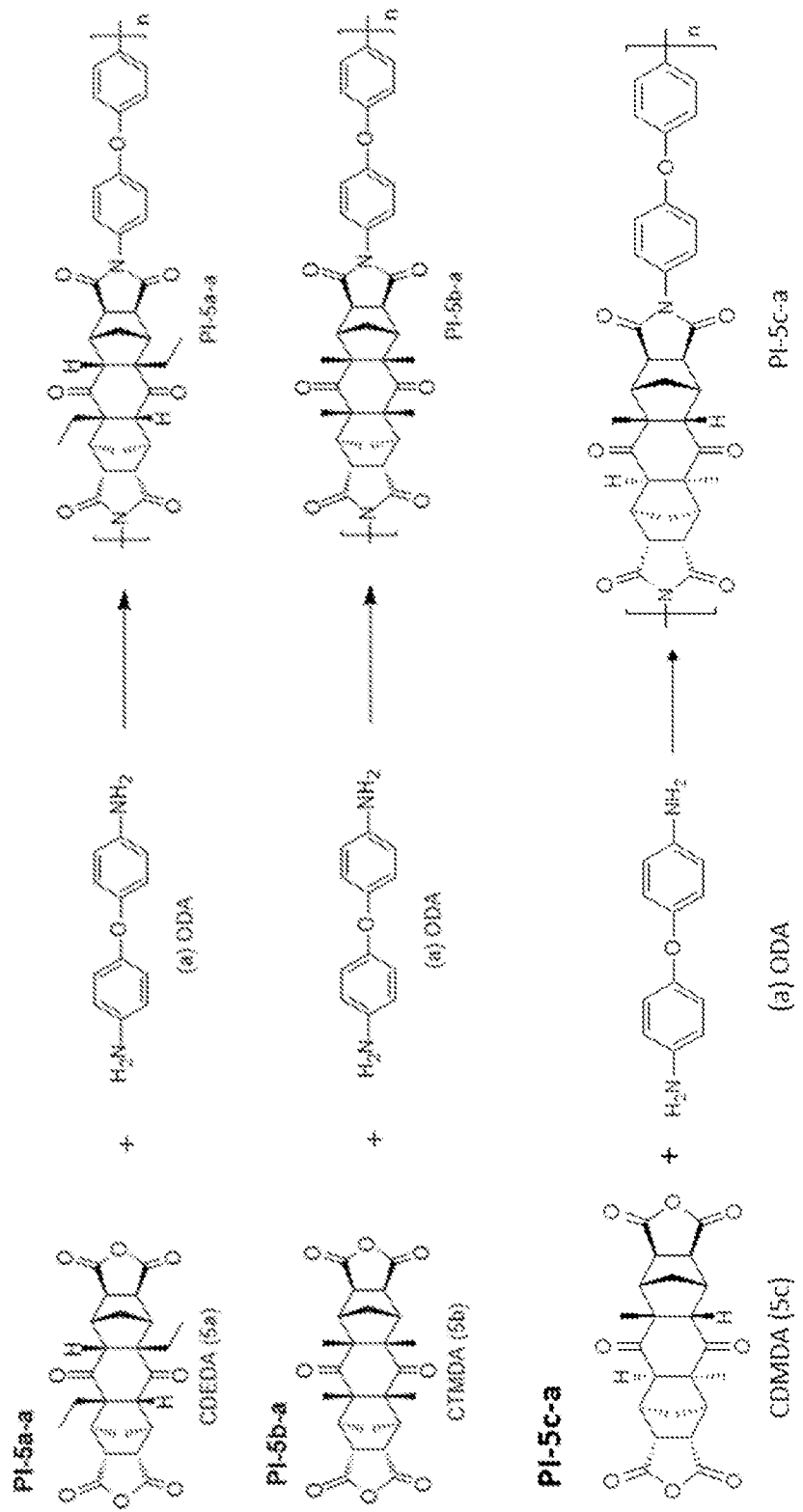
FIG. 2 and FIG. 3 are flow chart showing a preferable embodiment of the synthesis process for producing polyimide using the novel ketone-containing alicyclic dianhydrides series monomers with diamine in accordance with the present invention.
Figure 3:
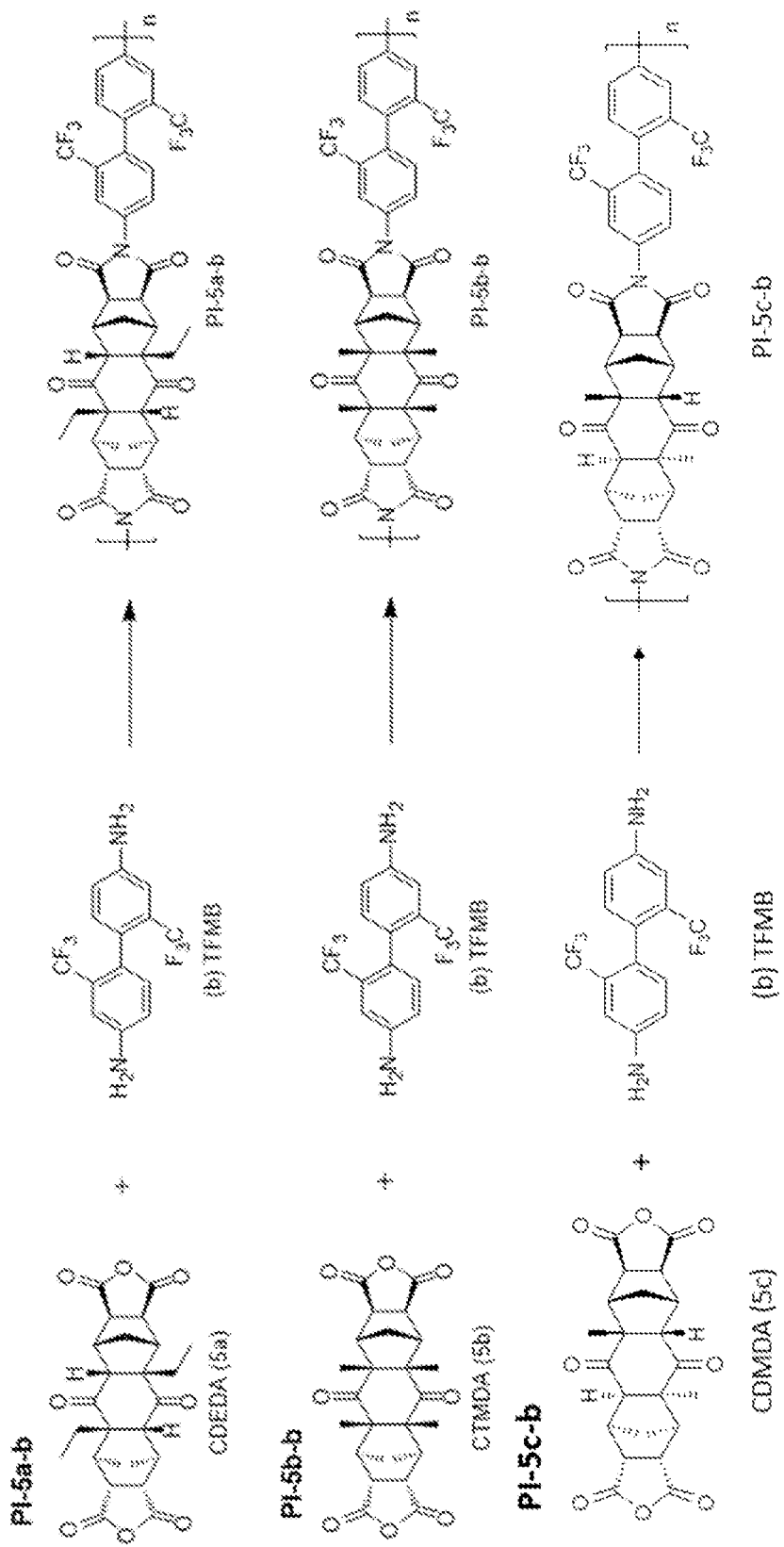

Furthermore, the polyimide polymers were synthesized by using the above-mentioned series of chemical compounds 5a, 5b and 5c. With reference to FIGS. 2 and 3, in these steps of the synthesis of the PI polymer, such as Formula (1), the R5 functional group in Formula (1) can be synthesized by using any aromatic diamines or aliphatic diamines such as 4,4'-oxydianiline (ODA) or 2,2'-bis (trifluoromethyl)-4,4'-diaminobiphenyl (2,2'-bis (trifluoromethyl)benzidine, TFMB) by one-step polymerization method.

1. As shown in FIG. 2, a polyimide was synthesized by one-step polymerization with 4,4'-oxydianiline (ODA) as a source of diamine monomer. The one-step polymerization of compounds 5a (CDEDA), 5b (CTMDA) and 5c (CDMDA) as alicyclic dianhydrides and ODA as aromatic diamines was taken as an example.

A 25 mL three-necked flask with fluxing of nitrogen, condenser tube and mechanical stirrer were installed. After adding 0.3273 3 g (1.63 mmol) ODA to the flask, 10.4 mL m-cresol after dehydrating distillation with phosphorus pentoxide was added to make the total solid content of the reaction solution as 10% (w/v). After stirring at room temperature, 0.7200 g (1.63 mmol) CTMDA was added into the solution, and the temperature was raised to 80° C. to make the solid completely dissolve, and the stirring was continued at this temperature for 8 hours. Then, the reaction temperature was raised to 200° C. and stirred quickly. After the reaction, the temperature of the solution was decreased to room temperature, and the solution was poured into methanol to precipitate. The white solids on the filter cake were collected by filtration. After extraction with ethanol using Soxhlet extractor and drying in 200° C. vacuum oven, 0.89 g of white solid was obtained with a yield of 90.5%. The resulting PI polymer with two variants of structure of PI-5a-a and PI-5b-a are shown in FIG. 2.

On the other hand, PI with structure of 5c (CDMDA) was add as 0.5000 g (2.50 mmol) of dried ODA into a 25 mL three-neck flask fluxing with nitrogen, condenser tube and mechanical stirrer. Then add 5 mL m-cresol after dehydrating distillation with phosphorus pentoxide. 0.6548 g (2.50 mmol) of CDMDA was added into the reaction solution, and all the anhydride was washed into the solution with 6 mL of m-cresol after dehydrating and distilling phosphorus pentoxide, so that the total solid content of the reaction solution was 10% (w/v). The temperature was raised to 80° C. and the solid was stirred at this temperature for 4.5 hours to dissolve completely. Then the catalyst, isoquinoline, 0.1 mL was added and the reaction temperature was raised to 200° C. and the solid was stirred quickly. After the reaction, the temperature of the solution was slowly decreased to room temperature and add m-cresol for dilution to ensure smooth mixing. Pour the solution into methanol to precipitate. Filter and collect the white filamentous solid on the filter cake. After Soxhlet extraction with ethanol and drying in vacuum oven at 200° C., white solid 1.0851 g was obtained with a yield of 93.96%. The resulting PI polymer with structure of PI-5c-a is shown in FIG. 2.

2. A one-step polymerization using 2,2'-bis (trifluoromethyl)-4,4'-diaminylbiphenyl (TFMB) as diamine monomer is shown in FIG. 3. The one-step polymerization of compounds 5a (CDEDA), 5b (CTMDA) and 5c (CDMDA) as alicyclic dianhydride and TFMB as one of aromatic diamines were taken as an example.

A 25 mL three-necked flask fluxing with nitrogen, condenser tube and mechanical stirrer were installed for reaction. The dried TFMB 0.7270 g (2.27 mmol) was added into the flask, and 17.3 mL m-cresol after dehydrating distillation with phosphorus pentoxide was added to make the total solid content of the reaction solution as 10% (w/v). After stirring at room temperature, 1.0000 g (2.27 mmol) CTMDA was added into the reaction solution, and the temperature was raised to 80° C. to make the solid completely dissolve. The solution was stirred at the same temperature for 1 hour. Then, the reaction temperature was raised to 200° C. and the reaction was quickly stirred for 2 days. After the reaction, the temperature of the solution was decreased to room temperature, and the solution was poured into methanol to precipitate. The white solids on the filter cake were collected by filtration. After extraction with ethanol using Soxhlet extractor and drying in 200° C. vacuum oven, 1.32 g white solid was obtained with 88.5% total yield. The resulting PI polymer with structures of PI-5a-b, PI-5b-b, and PI-5c-b are as shown in FIG. 3.

The polymer structures obtained in each embodiment of PI as mentioned above contain stereoisomers as in Formula (2) and (3).

Next, the present invention uses the PI polymer synthesized as aforementioned to prepare a polymer film. The polymerized polyimide was dissolved in GBL (γ-butyrolactone) with a solid content of 10% (w/v). Further filtering by 0.45 μm Teflon filter, pouring on dishes treated with isopropyl alcohol surface and baking in an circling oven at 80, 160, 200, 180, 150, 120, 90, 60° C. for one hour each individually and bake in a vacuum oven at 200° C. for 8 hours. After solvent drying, the film will leave the dish by itself.

Meanwhile, other better embodiments of the present invention can also dissolve the PI-5c-a polyimide polymer with a solid content of about 1.3% (w/v) in GBL. After being filtered by 0.45 μm Teflon filter, it was poured on dishes treated with isopropanol. After defoaming, it was baked in a circulating oven at 80, 160, 200, 180, 150, 120, 90, 60° C. for 1 hour each, and then baked in a vacuum oven at 200° C. for 8 hours. After drying with solvent, the film was gently removed from the dish to obtain the transparent polyimide polymer film with thickness of about 5~10 μm.

Series of verification tests of the PI polymer will be described as below.

With reference to Chart 2 as below, the results of the intrinsic viscosity, molecular weight and yield of the PI polymer in the present invention are presented wherein η(dL/g) in Chart 2 was tested using a polymer concentration of 0.5 g/dL, NMP in temperature of 35° C.

CHART 2

The same embodiment may be tested or compared in multiple groups for validating different abilities.

| Polymer | Viscosity η(dL/g) | Molecular weight Mw (kDa) | Molecular weight Mn (kDa) | Molecular weight distribution index PDI Mw/Mn | Yield (%) |
|---|---|---|---|---|---|
| PI-5a-a-1 | 0.40 | 55.0 | 34.0 | 1.62 | 100.1% |
| PI-5a-b-1 | 0.29 | 45.0 | 22.0 | 2.05 | 72.2% |
| PI-5b-a-1 | 0.25 | 36.0 | 16.0 | 2.25 | 90.5% |
| PI-5b-b-1 | 0.21 | 39.0 | 24.5 | 1.59 | 90.1% |
| PI-5c-a-1 | N/A | 384.0 | 189.0 | 2.03 | 94.0% |

With reference to Chart 3 below for the PI Polymer Solubility Test, 20 mg of each sample was added to 1 ml solvent and stirred to test the solubility. The symbol "+" means to dissolve when heated, "++" means to dissolve at room temperature, and "−" means not to dissolve when heated.

CHART 3

| Polymer | m-cresol | GBL | NMP | DMAc | DMSO | THF | $CHCl_3$ | Acetone |
|---|---|---|---|---|---|---|---|---|
| PI-5a-a | ++ | ++ | ++ | ++ | ++ | − | − | − |
| PI-5a-b | ++ | ++ | ++ | ++ | ++ | ++ | + | ++ |
| PI-5b-a | ++ | ++ | ++ | ++ | ++ | − | − | − |
| PI-5b-b | ++ | ++ | ++ | ++ | ++ | ++ | + | ++ |

With reference to below Chart 4, thermal properties of PI polymers of the present invention are shown where CTE was measured in the range of 50-150° C., Unit=μm $m^{-1}$ $°C.^{-1}$, and Tg was tested by TMA.

CHART 4

| Polymer | CTE | Tg (° C.) | $Td_{5\%}$ (° C.) | $Td_{10\%}$ (° C.) |
|---|---|---|---|---|
| PI-5a-a | 42.4 | >270 | 415.5 | 427.5 |
| PI-5a-b | NA (The film is too fragile to be tested) | NA (The film is too fragile to be tested) | 423.7 | 440.6 |
| PI-5b-a | 38.8 | 460 | 470.0 | 478.5 |
| PI-5b-b | NA The film is too fragile to be tested | (The film is too fragile to be tested) | 481.2 | 488.2 |
| PI-5c-a | 25.7 | 423 | 440.5 | 446.9 |

With reference to Chart 5 below, the mechanical properties of PI polymer in the present invention are shown.

CHART 5

| Polymer PI-5b-a | Thickness (μm) | Young's modulus (GPa) | Tensile Strength (MPa) | Tensile Strain (%) |
|---|---|---|---|---|
| PI-5b-a | 11 | 1.63 | 36.3 | 5.22 |
| PI-5b-a | 11 | 1.65 | 34.9 | 6.71 |
| PI-5b-a | 10 | 1.95 | 36.2 | 4.16 |
| PI-5b-a | 10 | 1.58 | 31.9 | 7.62 |
| PI-5b-a | 11 | 1.51 | 36.0 | 6.56 |
| Average | — | 1.66 | 35.1 | 6.05 |

Figure 14:
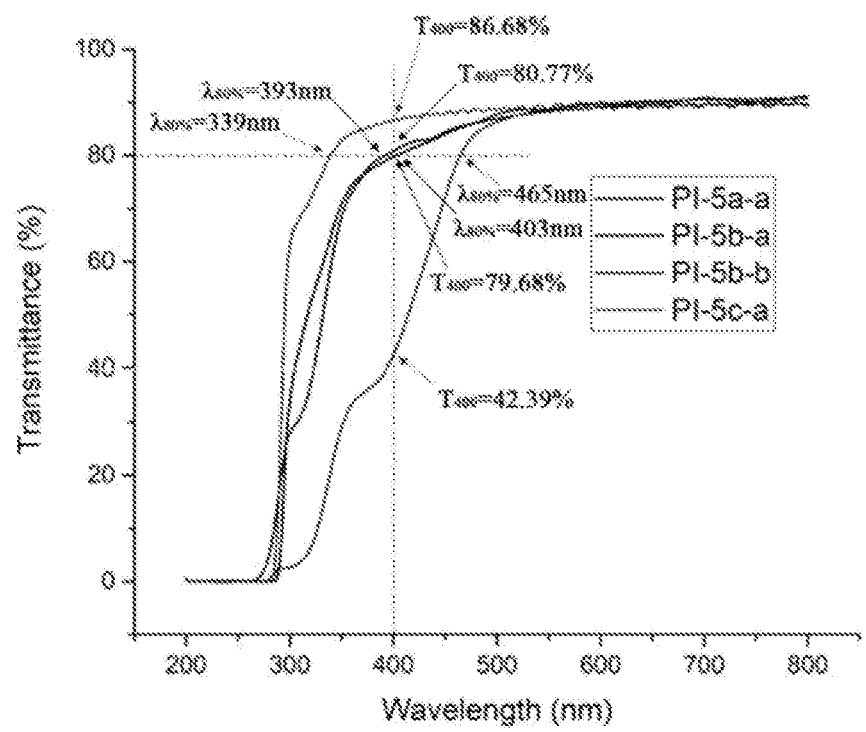
FIG. 14 is a UV-Vis spectroscopy of PI polymer film in accordance with the present invention.

With reference to below Chart 6 and FIG. 14, a UV-Vis spectroscopy of PI polymer films is shown.

CHART 6

$\lambda_{80\%}$ represents the wavelength at which the light transmittance of the film is 80%, $\lambda_{cut-off}$ represents the wavelength at which the light transmittance of the film is less than 1%, and $T_{400}$ (%) represents the light transmittance at the wavelength of 400 nm.

| Polymer | Thickness (μm) | $\lambda_{80\%}$ | $\lambda_{cut-off}$ | $T_{400}$ (%) |
|---|---|---|---|---|
| PI-5a-a | 12 μm | 393 nm | 271 nm | 80.77% |
| PI-5b-a | 14 μm | 403 nm | 288 nm | 79.68% |
| PI-5b-b | 28 μm | 465 nm | 281 nm | 42.39% |
| PI-5c-a | 12 μm | 339 nm | 284 nm | 86.68% |

With reference to Chart 7 below, an optical property test of PI polymer film is presented. In Chart 7, 400 nm and 550 nm represent a transmittance of polymer at wavelength of 400 nm and 550 nm respectively.

CHART 7

| Polymer | Thickness (μm) | Brightness 0—Black 100—White | Red (+)/ Green (−) | Yellow (+)/ Blue (−) | YI ASTM E313-05 (D65) | YI ASTM D1925 | 400 nm | 550 nm |
|---|---|---|---|---|---|---|---|---|
| Blank | — | 99.99 | 0 | 0 | 0 | 0.22 | 99.89 | 99.98 |
| PI-5b-a | 11 | 95.56 | −0.53 | 2.71 | 4.72 | 4.99 | 80.98 | 89.07 |
| PI-5b-a | 34 | 94.55 | −1.48 | 8.08 | 13.9 | 14.27 | 64.8 | 86.95 |
| PI-5b-a | 45 | 90.88 | −2.55 | 16.56 | 28.33 | 28.92 | 38.69 | 78.51 |

With reference to Chart 8 below, optical properties of PI polymer films are presented.

CHART 8

In chart 8, $R_{th}$ and $R_0$ are tested by spectrophotometer mainly calculated as Out-of-Plane and In-Plane conditions. $\Delta nb$ is calculated by the equation of $R_{th} = \Delta n * d$

| Polymer | Thickness (nm) | Out-of-plane retardation $R_{th}$ (nm) | Plane refractive index difference $\Delta nb$ | In-plane Retardation $R_0$ (nm) |
|---|---|---|---|---|
| PI-5b-a | 11000 | −14.7 | −0.0013 | 5.0 |
| PI-5b-a | 34000 | 135.1 | 0.0040 | 5.4 |
| PI-5b-a | 45000 | 139.4 | 0.0031 | 0.2 |

The above specification, examples, and data provide a complete description of the present disclosure and use of exemplary embodiments. Although various embodiments of the present disclosure have been described above with a certain degree of particularity, or with reference to one or more individual embodiments, those with ordinary skill in the art could make numerous alterations or modifications to the disclosed embodiments without departing from the spirit or scope of this disclosure.

What is claimed is:

1. A polyimide comprises at least one of below repeated structures as formula (1) and formula (2):

formula (1)

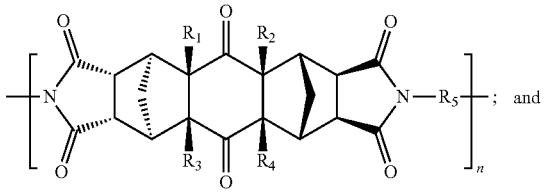

formula (2)

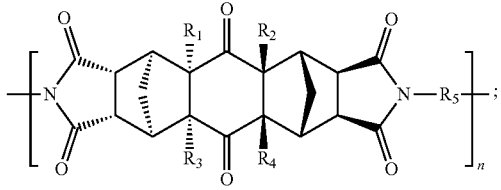

wherein in formula (1) or in formula (2):
R1, R2, R3 and R4 represent hydrogen atom and/or carbon containing functional group including C1 to C4 alkanes;
R5 represents aliphatic group or aromatic group; and
n represents any positive integer.

2. The polyimide as claimed in claim 1, wherein the aliphatic group comprises aliphatic diamine or aromatic group comprises aromatic diamine.

3. The polyimide as claimed in claim 2, wherein the aromatic diamine and aliphatic diamine comprise 4,4'-bis(aminophenyl)ether and 2,2'-bis(trifluoromethyl)benzidine.

4. A membrane, film or coat comprise polyimide as claimed in claim 1.

5. A membrane, film or coat comprise polyimide as claimed in claim 2.

* * * * *